(12) United States Patent
Martynova et al.

(10) Patent No.: US 12,156,817 B2
(45) Date of Patent: Dec. 3, 2024

(54) STANDALONE INTERBODY IMPLANTS

(71) Applicant: GLOBUS MEDICAL, INC., Audubon, PA (US)

(72) Inventors: Veronika Martynova, Aston, PA (US); Jason Zappacosta, Philadelphia, PA (US); Michael Hunt, Austin, TX (US); Jason Gray, East Greenville, PA (US); Jennifer Klimek, Paducah, KY (US); Noah Hansell, King of Prussia, PA (US); David Paul, Phoenixville, PA (US); Nick Padovani, Wynnewood, PA (US)

(73) Assignee: Globus Medical Inc., Audubon, PA (US)

( * ) Notice: Subject to any disclaimer, the term of this patent is extended or adjusted under 35 U.S.C. 154(b) by 93 days.

(21) Appl. No.: 17/658,703

(22) Filed: Apr. 11, 2022

(65) Prior Publication Data

US 2022/0233328 A1  Jul. 28, 2022

Related U.S. Application Data

(63) Continuation of application No. 16/732,393, filed on Jan. 2, 2020, now Pat. No. 11,331,201, which is a
(Continued)

(51) Int. Cl.
*A61F 2/44* (2006.01)
*A61F 2/28* (2006.01)
*A61F 2/30* (2006.01)

(52) U.S. Cl.
CPC .............. *A61F 2/447* (2013.01); *A61F 2/442* (2013.01); *A61F 2002/2835* (2013.01);
(Continued)

(58) Field of Classification Search
CPC .......... A61F 2/44; A61F 2/4405; A61F 2/442; A61F 2/4455; A61F 2/447;
(Continued)

(56) References Cited

U.S. PATENT DOCUMENTS 4,950,296 A * 8/1990 McIntyre .................. A61F 2/28
606/76
5,397,364 A 3/1995 Kozak et al.
(Continued)

FOREIGN PATENT DOCUMENTS

FR  2727003 A1  5/1996
JP  2011502708 A  1/2011
(Continued)

OTHER PUBLICATIONS

U.S. Appl. No. 60/777,663, filed Feb. 27, 2006, Messerli.
(Continued)

*Primary Examiner* — Anu Ramana

(57) ABSTRACT

Stand-alone interbody fusion devices for engagement between adjacent vertebrae. The stand-alone interbody fusion devices may include frames and one or more endplates coupled to the frame. The frame may be configured and designed to provide the apertures which are designed to retain bone fasteners, such as screws or anchors, and secure the implant to the adjacent vertebrae.

17 Claims, 34 Drawing Sheets

Related U.S. Application Data continuation of application No. 15/967,626, filed on May 1, 2018, now Pat. No. 10,537,438, which is a continuation of application No. 15/277,044, filed on Sep. 27, 2016, now Pat. No. 9,980,826, which is a continuation of application No. 14/556,345, filed on Dec. 1, 2014, now Pat. No. 9,486,327, which is a continuation-in-part of application No. 14/278,898, filed on May 15, 2014, now Pat. No. 9,545,320.

(52) U.S. Cl.
CPC ............ *A61F 2002/30014* (2013.01); *A61F 2002/3008* (2013.01); *A61F 2002/302* (2013.01); *A61F 2002/30202* (2013.01); *A61F 2002/30331* (2013.01); *A61F 2002/30387* (2013.01); *A61F 2002/3039* (2013.01); *A61F 2002/30403* (2013.01); *A61F 2002/30433* (2013.01); *A61F 2002/30482* (2013.01); *A61F 2002/30487* (2013.01); *A61F 2002/305* (2013.01); *A61F 2002/30571* (2013.01); *A61F 2002/30578* (2013.01); *A61F 2002/30607* (2013.01); *A61F 2002/30616* (2013.01); *A61F 2002/30787* (2013.01); *A61F 2002/30822* (2013.01); *A61F 2002/30823* (2013.01); *A61F 2002/30828* (2013.01); *A61F 2002/30843* (2013.01); *A61F 2310/00011* (2013.01); *A61F 2310/00023* (2013.01); *A61F 2310/00131* (2013.01); *A61F 2310/00359* (2013.01)

(58) Field of Classification Search
CPC .............. A61F 2002/4475; A61F 2/446; A61F 2/4465; A61F 2002/4415
See application file for complete search history.

(56) References Cited

U.S. PATENT DOCUMENTS

| | | | |
|---|---|---|---|
| 5,458,641 A | 10/1995 | Jiminez | |
| 5,549,612 A | 8/1996 | Yapp et al. | |
| 5,861,041 A | 1/1999 | Tienboon | |
| 5,888,223 A | 3/1999 | Bray, Jr. | |
| 6,066,175 A | 5/2000 | Henderson et al. | |
| 6,156,037 A | 12/2000 | LeHuec et al. | |
| 6,200,347 B1 | 3/2001 | Anderson et al. | |
| 6,206,922 B1 | 3/2001 | Zdeblick et al. | |
| 6,231,610 B1 | 5/2001 | Geisler | |
| 6,235,033 B1 | 5/2001 | Brace et al. | |
| 6,258,089 B1 | 7/2001 | Campbell et al. | |
| 6,383,186 B1 | 5/2002 | Michelson | |
| 6,432,106 B1 | 8/2002 | Fraser | |
| 6,458,158 B1* | 10/2002 | Anderson ............ A61F 2/28 623/16.11 |
| 6,482,233 B1 | 11/2002 | Aebi | |
| 6,540,785 B1 | 4/2003 | Gill et al. | |
| 6,558,423 B1 | 5/2003 | Michelson | |
| 6,558,424 B2 | 5/2003 | Thalgott | |
| 6,666,889 B1 | 12/2003 | Commarmond | |
| 6,682,563 B2 | 1/2004 | Scharf | |
| 6,740,118 B2 | 5/2004 | Eisermann et al. | |
| 6,827,740 B1 | 12/2004 | Michelson | |
| 6,899,735 B2 | 5/2005 | Coates et al. | |
| 6,902,578 B1* | 6/2005 | Anderson .......... A61L 27/3608 623/16.11 |
| 6,972,019 B2 | 12/2005 | Michelson | |
| 7,001,432 B2 | 2/2006 | Keller et al. | |
| 7,025,787 B2 | 4/2006 | Bryan et al. | |
| 7,137,997 B2 | 11/2006 | Paul | |
| 7,147,665 B1 | 12/2006 | Bryan et al. | |
| 7,153,325 B2 | 12/2006 | Kim et al. | |
| 7,172,627 B2 | 2/2007 | Fiere et al. | |
| 7,232,464 B2 | 6/2007 | Mathieu et al. | |
| 7,276,082 B2 | 10/2007 | Zdeblick et al. | |
| 7,309,357 B2 | 12/2007 | Kim | |
| 7,320,708 B1 | 1/2008 | Bernstein | |
| 7,618,456 B2 | 11/2009 | Mathieu et al. | |
| 7,771,475 B2 | 8/2010 | Michelson | |
| 7,846,207 B2 | 12/2010 | Lechmann et al. | |
| 7,862,616 B2 | 1/2011 | Lechmann et al. | |
| 7,875,076 B2 | 1/2011 | Mathieu et al. | |
| 8,100,976 B2 | 1/2012 | Bray et al. | |
| 8,137,403 B2 | 3/2012 | Michelson | |
| 8,343,222 B2 | 1/2013 | Cope | |
| 8,486,149 B2 | 7/2013 | Saidha et al. | |
| 8,540,774 B2 | 9/2013 | Kuenzi et al. | |
| 8,685,099 B2* | 4/2014 | Bhattacharya ........ A61F 2/4455 623/17.11 |
| 2002/0010511 A1 | 1/2002 | Michelson | |
| 2002/0016595 A1 | 2/2002 | Michelson | |
| 2003/0045939 A1 | 3/2003 | Casutt | |
| 2003/0105528 A1 | 6/2003 | Shimp et al. | |
| 2003/0125739 A1 | 7/2003 | Bagga et al. | |
| 2003/0167091 A1 | 9/2003 | Scharf | |
| 2004/0078078 A1 | 4/2004 | Shepard | |
| 2004/0143270 A1 | 7/2004 | Zucherman et al. | |
| 2004/0143332 A1 | 7/2004 | Krueger et al. | |
| 2004/0176853 A1 | 9/2004 | Sennett et al. | |
| 2005/0055098 A1 | 3/2005 | Zdeblick et al. | |
| 2005/0065607 A1 | 3/2005 | Gross | |
| 2005/0149192 A1 | 7/2005 | Zucherman et al. | |
| 2005/0149193 A1 | 7/2005 | Zucherman et al. | |
| 2005/0159819 A1 | 7/2005 | McCormack et al. | |
| 2005/0171607 A1 | 8/2005 | Michelson | |
| 2005/0177236 A1 | 8/2005 | Mathieu et al. | |
| 2005/0187625 A1 | 8/2005 | Wolek et al. | |
| 2005/0240267 A1 | 10/2005 | Randall et al. | |
| 2005/0240271 A1 | 10/2005 | Zubok et al. | |
| 2005/0256574 A1 | 11/2005 | Paul et al. | |
| 2006/0085071 A1 | 4/2006 | Lechmann et al. | |
| 2006/0116767 A1 | 6/2006 | Magerl et al. | |
| 2006/0129240 A1 | 6/2006 | Lessar et al. | |
| 2006/0195191 A1* | 8/2006 | Sweeney, II .......... A61F 2/4611 623/17.13 |
| 2006/0217809 A1 | 9/2006 | Albert et al. | |
| 2007/0088441 A1 | 4/2007 | Duggal et al. | |
| 2007/0123987 A1 | 5/2007 | Bernstein | |
| 2007/0135923 A1 | 6/2007 | Peterman et al. | |
| 2007/0162130 A1 | 7/2007 | Rashbaum et al. | |
| 2007/0168032 A1 | 7/2007 | Muhanna et al. | |
| 2007/0225806 A1 | 9/2007 | Squires et al. | |
| 2007/0225812 A1 | 9/2007 | Gill | |
| 2007/0233253 A1 | 10/2007 | Bray et al. | |
| 2007/0250167 A1 | 10/2007 | Bray et al. | |
| 2007/0270961 A1 | 11/2007 | Ferguson | |
| 2008/0046083 A1 | 2/2008 | Hewko | |
| 2008/0051890 A1 | 2/2008 | Waugh et al. | |
| 2008/0051907 A1 | 2/2008 | Marik | |
| 2008/0133013 A1 | 6/2008 | Duggal et al. | |
| 2008/0281425 A1 | 11/2008 | Thalgott et al. | |
| 2009/0076608 A1 | 3/2009 | Gordon et al. | |
| 2009/0210062 A1 | 8/2009 | Thalgott et al. | |
| 2010/0042216 A1 | 2/2010 | Kilpela et al. | |
| 2010/0057206 A1 | 3/2010 | Duffield et al. | |
| 2010/0087925 A1 | 4/2010 | Kostuik et al. | |
| 2010/0312345 A1 | 12/2010 | Duffield et al. | |
| 2010/0312346 A1 | 12/2010 | Kuenzi et al. | |
| 2012/0078371 A1 | 3/2012 | Gamache et al. | |
| 2012/0078373 A1 | 3/2012 | Gamache et al. | |
| 2012/0179259 A1 | 7/2012 | McDonough et al. | |
| 2012/0290089 A1 | 11/2012 | Melamed | |
| 2014/0039623 A1 | 2/2014 | Iott et al. | |
| 2014/0228957 A1 | 8/2014 | Niemiec et al. | |
| 2014/0257487 A1 | 9/2014 | Lawson et al. | |
| 2014/0277489 A1 | 9/2014 | Davenport et al. | |
| 2014/0277497 A1 | 9/2014 | Bennett et al. | |
| 2014/0309741 A1 | 10/2014 | Ganter et al. | |
| 2014/0336770 A1 | 11/2014 | Petersheim et al. | |
| 2015/0190241 A1 | 7/2015 | Gowan | |
| 2015/0328009 A1 | 11/2015 | Zappacosta et al. | |

(56) References Cited

U.S. PATENT DOCUMENTS

FOREIGN PATENT DOCUMENTS

| JP | 2013-540503 A | 11/2013 |
| JP | 2016512110 A | 4/2016 |
| JP | 2017501835 A | 1/2017 |
| WO | 1997023175 A1 | 7/1997 |
| WO | 1999063914 A1 | 12/1999 |
| WO | 2005007040 A1 | 1/2005 |
| WO | 2007098288 A2 | 8/2007 |
| WO | 2008014258 A2 | 1/2008 |
| WO | 2012115631 A1 | 8/2012 |
| WO | 2014138311 A1 | 9/2014 |

OTHER PUBLICATIONS

U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, U.S. Dept. of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).
Synthes' SynFix Technique Guide device ("SynFix Technique Guide").

* cited by examiner

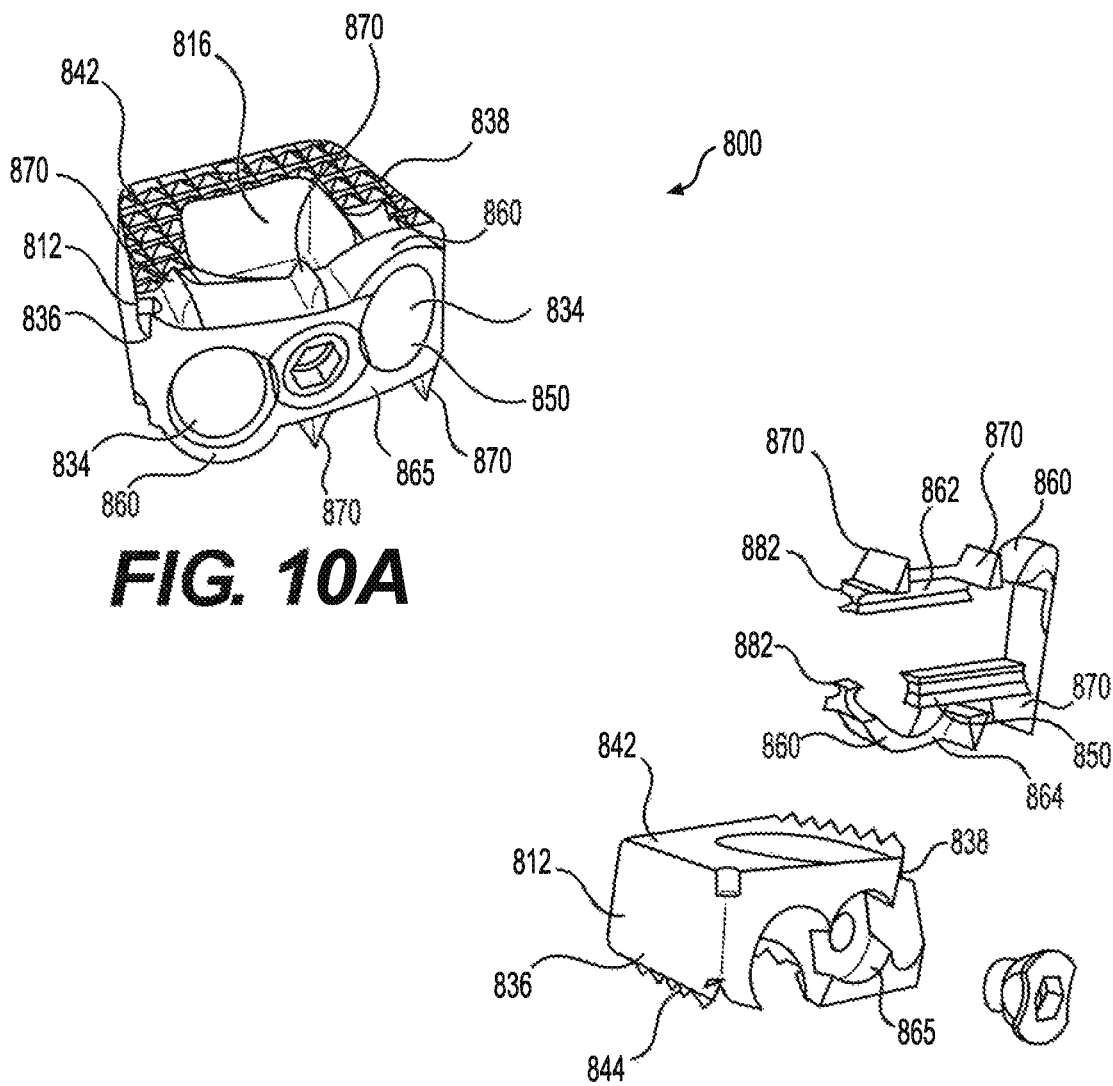
FIG. 10A
FIG. 10B
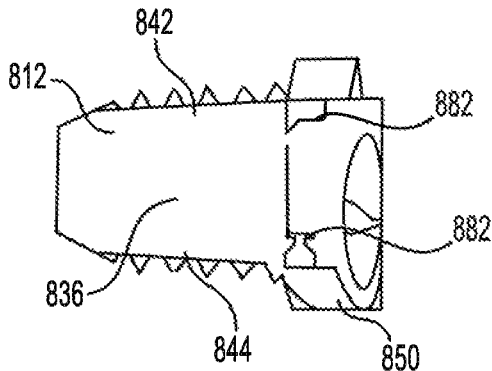
FIG. 10C

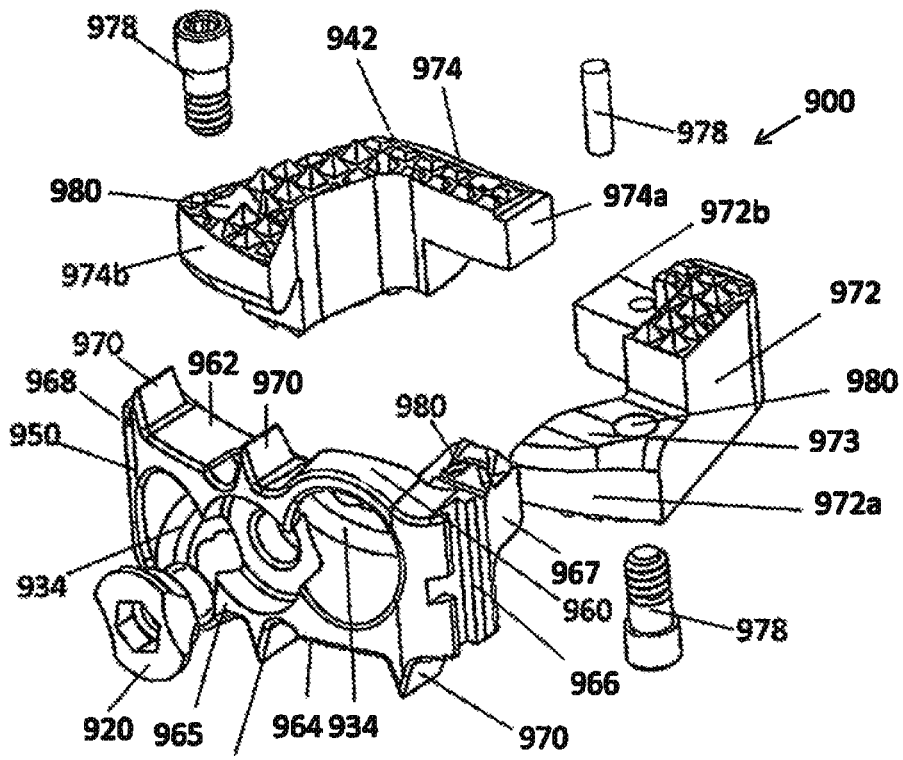
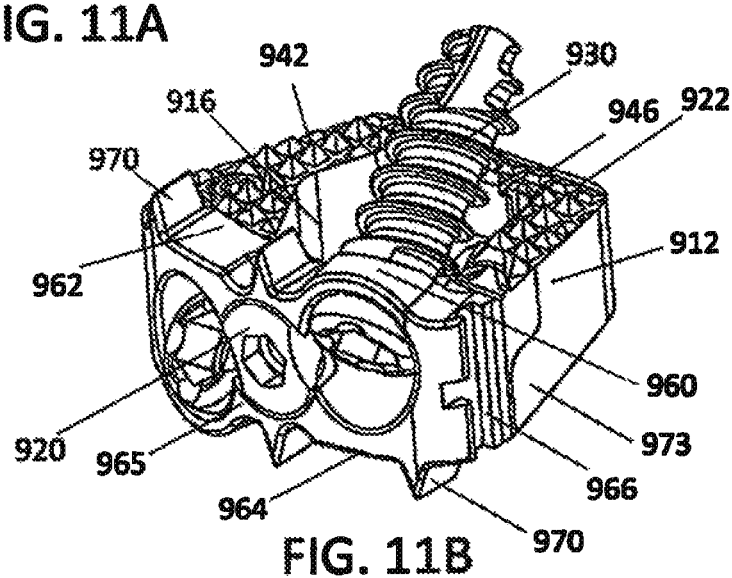
FIG. 11A
FIG. 11B

STANDALONE INTERBODY IMPLANTS

CROSS REFERENCE TO RELATED APPLICATION

The present application is a continuation of U.S. patent application Ser. No. 16/732,393, filed on Jan. 2, 2020, now issued as U.S. Pat. No. 11,331,201, which is a continuation of U.S. patent application Ser. No. 15/967,626 filed on May 1, 2018, now issued U.S. Pat. No. 10,537,438, which is a continuation of U.S. patent application Ser. No. 15/277,044 filed on Sep. 27, 2016, now issued U.S. Pat. No. 9,980,826, which is a continuation of U.S. patent application Ser. No. 14/556,345, filed Dec. 1, 2014, now issued U.S. Pat. No. 9,486,327, which is a continuation-in-part of U.S. patent application Ser. No. 14/278,898 filed on May 15, 2014, now issued U.S. Pat. No. 9,545,320, the entire disclosures of which are incorporated herein by reference in their entireties for all purposes.

FIELD OF THE INVENTION

The present disclosure generally relates to fixation devices for positioning and immobilizing adjacent vertebral bodies. In particular, the devices may include stand-alone interbody fusion devices.

BACKGROUND OF THE INVENTION

As people age, the intervertebral discs in the spinal column may start to deteriorate. Subsequently, the intervertebral discs being to lose height. As a result of the loss of height between vertebral bodies, the nerves exiting from the spinal canal become compressed and pinched, which causes pain among other neurological deficits. One solution is to insert a spacer in place of the disc to restore the height and to promote fusion between adjacent vertebral bodies to permanently maintain the height restoration. Additional fixation is also needed to stabilize the spinal segment. A plate is usually provided, and the plate may be positioned on the anterior portions of the adjacent vertebral bodies. In some cases, the profile of the plate becomes obstructive to the anatomy. The approach to the spine is also significant in that a direct anterior approach requires navigation or dissection of vascular anatomy.

As a result, there is a need to provide a spacer having fixation elements to attach the spacer directly to adjacent vertebrae, to limit any profile protruding out of the spine column anteriorly, and to avoid proximal anatomy from a direct anterior approach. The spacer alone, however, may not be strong enough to support fixation elements, such as screws, when the spacer is made solely from certain non-metallic materials, such as, polyether ether ketone (PEEK). Thus, there is also a need for frames or spacers at least partially constructed of strong materials or in such a manner so as to provide additional support for the fixation elements.

SUMMARY OF THE INVENTION

To meet this and other needs, stand-alone interbody fusion implants and devices are provided. The implants may be provided with a spacer and at least one insert or member. The implants may also be composed of a frame with one or more endplates affixed thereto. The inserts, members, or frames may be especially suited for defining apertures designed to secure fixation elements or fasteners, such as screws, staples, pins, nails, anchors, or the like, and the spacers to adjacent vertebrae. These implants provide for a spine stabilization system that promotes fusion of adjacent vertebrae while at the same time providing stabilization of the spinal area where fusion occurs.

According to one embodiment, an intervertebral implant for implantation in an intervertebral space between adjacent vertebrae includes a spacer and at least one insert. The spacer has a superior surface, an inferior surface, a proximal end, and a distal end. The superior surface and the inferior surface each have a contact area configured to engage adjacent vertebrae. The spacer defines an opening extending from the superior surface to the inferior surface of the spacer. The opening may be configured for receiving bone graft material to promote fusion of the adjacent vertebral bodies. The spacer defines one or more cutout extending from the proximal end to the opening. The spacer may also include a plurality of protrusions on the contact areas of the superior and inferior surfaces for engaging the adjacent vertebrae.

The insert at least partially defines a fastener aperture. These apertures may be in the form of through holes designed, sized, and dimensioned to accommodate and receive fixation devices or fasteners, such as bone screws or anchors. The insert is coupled to the spacer such that at least a portion of the insert is received in the cutout in the spacer.

The insert may be configured in such a way to enhance the strength and stability of the spacer. The insert may extend a distance beyond the superior surface, the inferior surface, or both surfaces of the spacer (e.g., a portion of the insert may extend above or below the superior and inferior surfaces of the spacer). For example, a front surface of the insert may include at least one eyebrow where the eyebrow projects past the superior surface, the inferior surface, or both surfaces of the spacer. The fastener aperture for receiving the fastener may traverse the front surface of the insert at an angle divergent to a horizontal plane in order to help secure the implant to one or both of the adjacent vertebrae.

Unlike a traditional plate, which is typically a thin, flat sheet or strip of material, the insert is provided with a given depth and dimension designed to integrate seamlessly with the spacer. In particular, the depth of the insert may be greater than the width and/or height of the insert. The insert may include a head portion and at least one arm projecting therefrom. The head portion may be enlarged to define the aperture configured for retaining the fastener. The arm may extend laterally, medially, and/or posteriorly away from the head portion. In particular, the arm may extend posteriorly and may be configured to mimic the shape and design of the spacer. The spacer may define at least one recess sized and dimensioned to retain at least a portion of the arm. For example, the arm may rest against a portion of the spacer or a recess therein to form a lap joint, half lap joint, stepped joint, or the like. Any type of joint formed between the insert and the spacer may be secured with one or more pins.

According to another embodiment, the insert may be provided in the shape of a ring, cylinder, c-shape, or the like. The ring or c-shaped insert may be provided with one or more slits, for example, to allow the insert to tightly mate with the cutout through the spacer and secure the insert to the spacer. In particular, one or more slits may be longitudinally positioned around a periphery of the ring or c-shaped insert.

According to yet another embodiment, a stand-alone implant for implantation in a treated area of an intervertebral space between vertebral bodies of a spine includes a spacer and at least one member. The spacer has a first spacer portion and a second spacer portion, each of the first and second spacer portions having a first end and a second end. The second end of the first spacer portion is coupled to the first end of the second spacer portion. The first and second spacer portions form a superior surface and an inferior surface, and the superior surface and the inferior surface each have a contact area configured to engage adjacent vertebrae.

The member has an upper surface, a lower surface, a first lateral portion, a second lateral portion, and at least one hole traversing the member for receiving a fastener. The member is coupled to the spacer such that the first end of the first spacer portion engages the first lateral portion of the member and the second end of the second spacer portion engages the second lateral portion of the member.

The first and second spacer portions may be joined together in any suitable manner. For example, the first and second spacer portions may be mated together by a splice joint, scarf joint, butt joint, or the like. In the alternative or in addition, the first and second spacer portions may be secured together with one or more connectors. For example, the connector may include at least first and second tenons sized and configured to be received within a first mortise in the second end of the first spacer portion and a second mortise in the first end of the second spacer portion. Any type of joint formed between the first and second spacer portions may be further secured with one or more pins or the like.

The spacer portions and the member may also be joined together in any suitable manner. Similar to the insert configuration, the member may rest against a portion of the spacer portions or a recess therein to form a lap joint, half lap joint, stepped joint, or the like. For example, the member may include a first extension extending from the first lateral portion and a second extension extending from the second lateral portion. The first extension may contact a first ledge on the first spacer portion to form a first half lap joint, and the second extension may contact a second ledge on the second spacer portion to form a second half lap joint. If desired, the first and second half lap joints may each be further secured with at least one pin.

According to a further embodiment, an implant for implantation in an intervertebral space between adjacent vertebrae includes a spacer and an anterior portion. The spacer has a superior surface, an inferior surface, a proximal end, and a distal end, configured for insertion into the intervertebral space. The superior surface and the inferior surface each have a contact area configured to engage adjacent vertebrae. The spacer defines an opening extending from the superior surface to the inferior surface of the spacer.

The anterior portion extends from the proximal end of the spacer such that the anterior portion and the spacer are a single piece. The anterior portion has an upper surface, a lower surface, a first lateral portion, a second lateral portion, and at least one hole traversing the anterior portion for receiving a fastener. At least a portion of the upper surface or the lower surface of the anterior portion extends beyond the superior surface or the inferior surface of the spacer. For example, at least one beam may connect the anterior portion to the proximal end of the spacer to form a unitary piece.

The distal end of the spacer may have a first spring feature configured to allow for compression and expansion of the spacer. For example, the first spring feature may be in the form of a v-spring. In addition, the proximal end of the spacer may include a second spring feature. The second spring feature may also be in the form of a v-spring. In particular, the second spring feature may include more than one v-spring oriented in opposite directions. The first and second spring features may be configured such that the spacer simulates the modulus of elasticity of bone even when the spacer and the anterior portion are comprised of titanium.

According to another embodiment, an intervertebral implant for implantation in an intervertebral space between adjacent vertebrae may include a frame and at least one endplate. The frame may include a front portion, a first arm extending from a first end of the front portion, and a second arm extending from a second end of the front portion. The front portion may at least partially define at least one fastener aperture sized and dimensioned for receiving a fastener, such as a bone screw or an anchor. The endplate includes at least one outer surface having a contact area configured to engage adjacent vertebrae. The endplate is affixed to the frame such that the endplate contacts at least a portion of the plurality arms.

The frame may include a support member positioned centrally between the first and second arms. The support member may define at least one opening to retain a corresponding protrusion on the which is configured to provide for a friction fit between the endplate and the frame. The opening may be elongated with a beveled perimeter such that a corresponding protrusion on the endplate is configured to be snapped into the opening in the support member. The endplate may also defines at least one indentation on a lateral portion of the endplate to retain a corresponding protrusion on the first and/or second arms which is also configured to provide an interference fit between the endplate and the frame. The first and second arms may join together at a rear portion to form a ring-like structure.

The endplates may include at least two endplates: a first endplate configured to fit in a first opening between the first arm and the support member and a second endplate configured to fit in a second opening between the second arm and the support member. The endplate may be inserted from the top, bottom, or back of the implant.

The front portion of the frame may be a unitary piece or may be divided into two separate portions with a passage positioned therebetween. The endplate may include a central portion sized and configured to fit within the passage in the front portion. The central portion may define an opening sized and configured to receive an insert which accepts an anti-backout locking mechanism. In addition to the central portion, the endplate may include a first lateral wing and a second lateral wing. The first lateral wing may be configured to contact a portion of the first arm (e.g., forming at least a portion of an upper surface of the implant) and the second lateral wing may be configured to contact a portion of the second arm (e.g., forming at least a portion of a lower surface of the implant).

According to yet another embodiment, the implant may include a frame having a superior surface, an inferior surface, a proximal end, and a distal end, wherein the superior surface and the inferior surface each have a contact area configured to engage adjacent vertebrae, and the frame defines at least one opening extending from the superior surface to the inferior surface of the frame. The frame includes a front surface defining at least one fastener aperture provided at an angle divergent to a horizontal plane for receiving a fastener. The endplates may be sized and configured to fit within the openings in the frame, where the endplates are coupled to the frame by an interference fit and a ridge projecting around an outer perimeter of the endplate sized and configured to be received within a corresponding slot located within the opening. The slot may be located, for example, on a mid-transverse plane of the frame.

In any of the embodiments described herein, the implant may also include a locking mechanism, for example, disposed on the spacer, insert, member, or frame for preventing back out of the screws. For example, a cam-style blocking mechanism may be used with screws that capture the fixation device screws once they are inserted fully into the implant.

The implants may be formed from any suitable biocompatible materials. For example, the implant may be manufactured from a biocompatible metal, such as titanium, polyether ether ketone (PEEK), bone or the like. In one embodiment, the spacer or endplates is formed of a first material and the insert, member, or frame is formed of a second material different from the first material. The insert, member, or frame may be made of a stronger material designed to strength and reinforce one or more openings in the spacer (e.g., designed to retain bone screws) or as attached to the endplates. For example, the spacer or endplates may be formed from PEEK and the insert, member, and frame may be formed from titanium. In the embodiment where the anterior portion and the spacer form a single piece, titanium may be selected for the entire implant because the one or more spring features provide for the spacer to emulate the elasticity of bone.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 10A is a perspective view of a tenth embodiment including a single insert with a clamp-like design;

FIG. 10B is an exploded view of the embodiment shown in FIG. 10A;

FIG. 10C is a lateral view of the embodiment shown in FIG. 10A;

FIG. 11A shows an exploded view of an eleventh embodiment including a two-part spacer and a member;

FIG. 11B shows a perspective view of the embodiment shown in FIG. 11A;

DETAILED DESCRIPTION OF THE INVENTION

Figure 1A:
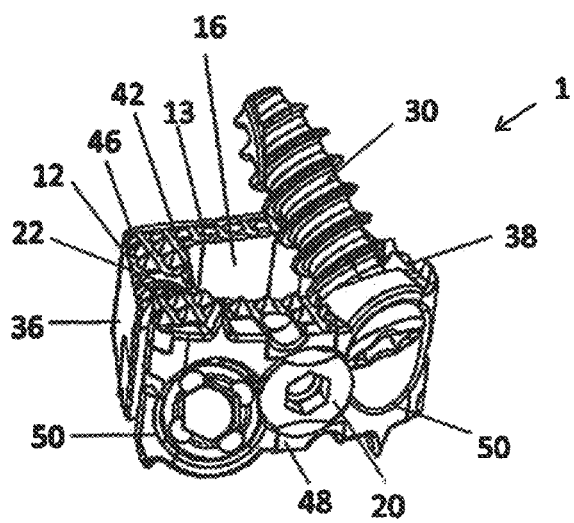
FIG. 1A is a perspective view of a first embodiment suitable for cervical interbody fusion including a spacer with inserts configured to retain bone fasteners when secure to adjacent vertebrae.

Embodiments of the disclosure are generally directed to stand-alone interbody fusion implants. Specifically, the implants include a spacer combined with at least one insert or member. The inserts or members may be included, for example, to provide openings such as through holes which are designed to retain bone fasteners, such as screws, anchors, staples, pins, nails, and the like. According to other embodiments, the implants include a frame combined with one or more endplates. The frame includes a portion with openings such as through holes which are designed to retain bone fasteners, such as screws, anchors, staples, pins, nails, and the like. The frame may also include arms and an optional support member designed to secure the endplates, for example, with an interference fit.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible areas.

FIGS. 1A-1E illustrate different views of one particular embodiment of the stand-alone intervertebral implant 1. As shown in the perspective view of FIG. 1A, the implant 1 includes a spacer 12 and one or more inserts 50. The inserts 50 may be especially designed and configured to define a fastener aperture 34 and/or stabilize, strengthen, and/or reinforce the spacer 12.

The spacer 12 includes a superior surface 42 and an inferior surface 44. The superior and inferior surfaces 42, 44 each have a contact area 22 configured to contact and engage adjacent vertebrae (not shown). The superior and inferior surfaces 42, 44 may be parallel, curved, or angled to help restore or recreate a lordosis angle (or other angle) of the human spine. In particular, the superior and inferior surfaces 42, 44 may have a convex curve on the upper and lower surfaces or may be angled from a distal end to a proximal end or from one lateral side to the other to account for curvature of the spine. In addition, the superior and/or inferior surfaces 42, 44 may be contoured to conform more closely to the concave endplates of the adjacent vertebra.

In order to engage the adjacent vertebrae, the spacer 12 may include a plurality of protrusions 13 or teeth on the contact areas 22 of the superior and/or inferior surfaces 42, 44. The protrusions 13 on the superior and inferior surfaces 42, 44 of each implant 1 grip the endplates of the adjacent vertebrae, resist migration, and aid in expulsion resistance. The plurality of protrusions 13 may be pyramidal in shape, but the protrusions 13 can be configured to be any size or shape to enhance anchoring the spacer 12 and the implant 1 to each of the adjacent vertebrae.

The implant 1 may contain an opening 16. The opening 16 may be in the form of an axial graft hole within the spacer 12 configured to provide the maximum amount of volume for bone graft packing. The opening 16 may be configured for receiving bone graft material, for example, to promote fusion of the adjacent vertebral bodies. The opening 16 may extend from the superior surface 42 to the inferior surface 44 of the spacer 12 to define a substantially hollow center suitable for retaining one or more bone graft materials. For example, cadaveric bone, autologous bone, bone slurry, BMP, or other similar materials, may enhance tissue growth within the intervertebral space.

The spacer 12 includes a distal end 46 and a proximal end 48. The distal end 46 of the spacer 12 may include a leading taper 40 for ease of insertion into the disc space. The leading taper 40 may be in the form of a chamfer or a bevel which enables self-distraction of the adjacent vertebral bodies during insertion of the implant 1. The leading taper 40 may be located along the insertion direction of the implant 1. For example, the leading taper 40 may assist in an anterior approach to the disc space.

Figure 1B:
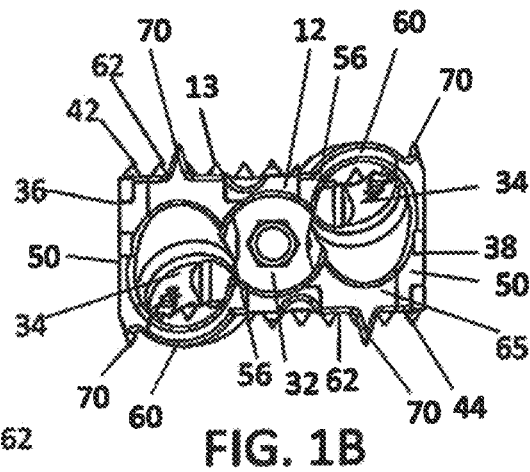
FIG. 1B is a front view of the embodiment shown in FIG. 1A.
Figure 1C:
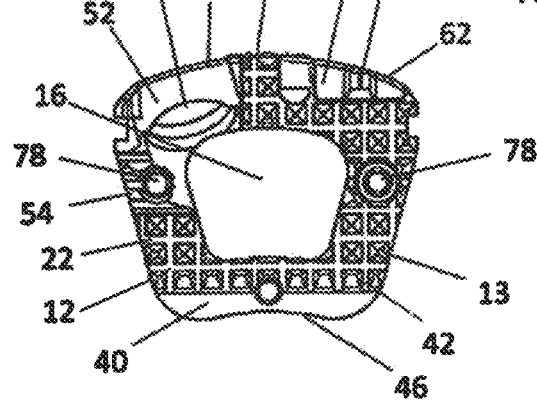
FIG. 1C is a top view of the embodiment shown in FIG. 1A.
Figure 1D:
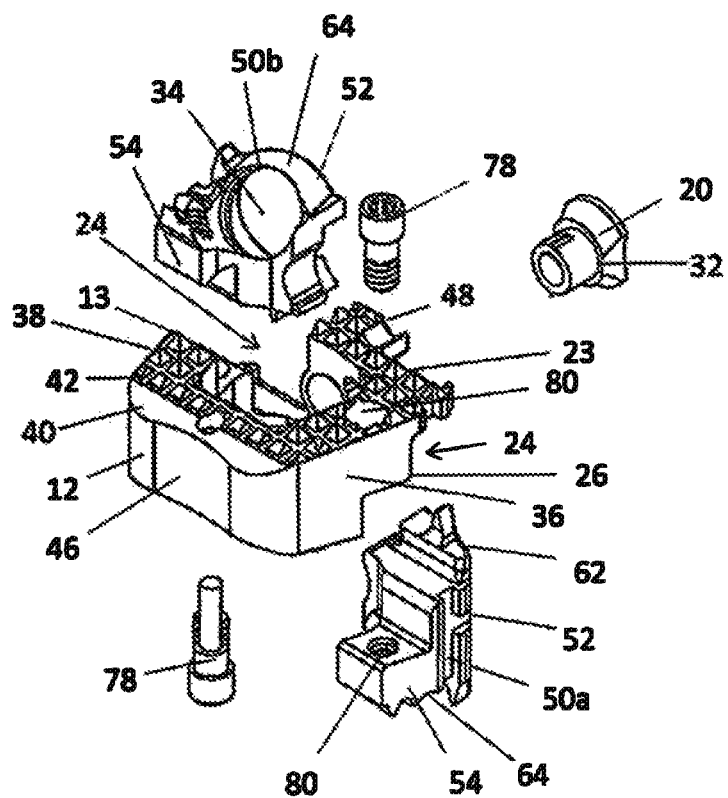
FIG. 1D is an exploded view of the embodiment shown in FIG. 1A.

As provided in FIG. 1D, the spacer 12 defines at least one cutout 24 extending from the proximal end 48 to the opening 16. In particular, the cutout 24 may be in fluid communication with the opening 16. The cutouts 24 may also be defined through a portion of the lateral sides 36, 38 to the opening 16. The cutouts 24 may be of any suitable shape and configuration, but are preferably sized and dimensioned to receive and retain at least a portion of the insert 50. For example, the cutout 24 may be sized and dimensioned to receive one or more faces or sides of the insert 50. The cutout 24 may be uniform or non-uniform and may comprise any morphology of recesses and protrusions configured to mate with the insert 50, for example, including a male/female mating. For example, the cutout 24 may be defined by one or more stepped projections 26 on the spacer 12. The cutout 24 may be defined such that the spacer 12 remains a single continuous piece (FIG. 1D) or the cutout 24 may be defined such that the spacer is broken into separate sections or pieces (not shown).

The insert 50 may be configured to comprise a fastener aperture 34, which is sized and dimensioned for receiving a fastener, such as a screw 30. Thus, the implant 1 may be secured to the adjacent vertebrae using fasteners, such as screws, anchors, staples, pins, nails, or the like.

The insert 50 is provided with a given depth and dimension designed to integrate seamlessly with the spacer 12. In particular, the depth of the insert 50 may be greater than the width and/or height of the insert 50. In addition, the insert 50 may not span across an entire frontage of the spacer 12. Instead, the inserts 50 may be provided as discrete units designed to marry with the spacer 12 only at locations needed to reinforce and/or position bone fasteners, such as screws 30. Thus, the inserts 50 may form only a portion of the front or an area proximate to the front of the implant 1. In the embodiment shown in FIG. 1A when two inserts 50 are present, the inserts 50 may be separated a distance apart with a portion of spacer 12 positioned between the two inserts 50.

A shown in FIG. 1D, the insert 50 may include a head portion 52 and at least one arm 54 projecting therefrom. The head portion 52 may be enlarged to define the opening or fastener aperture 34 configured for retaining the fastener. The head portion 52 may include a cylindrical portion forming the fastener aperture 34. The arm 54 may extend from the head portion 52 in one or more directions to contact and integrate with the spacer 12. For example, the arm 54 may extend laterally, medially, and/or posteriorly away from the head portion 52. In particular, the arm 54 may extend posteriorly away from the head portion 52 and toward the distal end 46 of the spacer 12 when attached thereto.

The insert 50 including a portion of the arm 54 and/or a portion of the head portion 52 may be configured to mirror the shape and design of the spacer 12. The spacer 12 may define at least one recess, projection, etc. sized and dimensioned to retain at least a portion of the arm 54. For example, the arm 54 or any portion of the insert 50 may rest against a portion of the spacer 12 or a recess formed therein to provide a joint, such as a lap joint, half lap joint, dovetail lap joint, beveled lap joint or scarf joint, stepped lap joint, tabled lap joint, or the like. In particular, a lap joint may include joining two pieces of material together by at least partially overlapping them (e.g., at least a portion of the insert 50 and a portion of the spacer 12 are overlapped). In a full lap, no material is removed from either of the members to be joined, resulting in a joint which is the combined thickness of the two members. In a half lap joint, material is removed from each of the members so that the resulting joint is the thickness of the thickest member. In the embodiment shown in FIG. 1E, the joint portion between the insert 50 and the spacer 12 is at least partially a half lap joint such that the joint does not increase the height of the spacer 12.

Figure 1E:
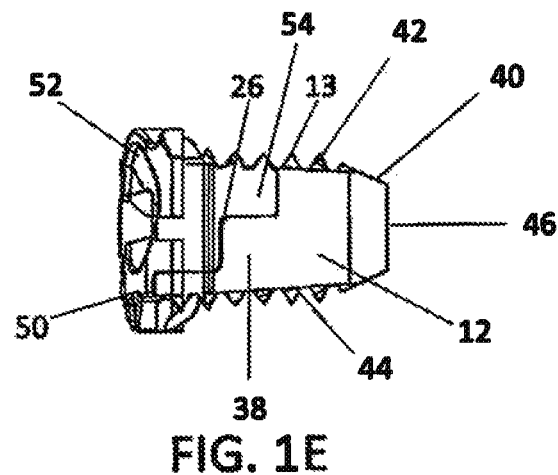
FIG. 1E is a lateral view of the embodiment shown in FIG. 1A.

As shown in FIG. 1E, the insert 50 may join the spacer 12 with a stepped lap joint. A portion of the insert 50 may be stepped with a male projection to mate with a stepped female configuration of the spacer 12. A series of offset planar surfaces having a rise and a run may form the stepped profile. For example, the arm 54 of the insert 50 may be stepped with a male projection configured to mate with corresponding stepped projections 26 on the spacer 12. Depending on the configuration of the joint, the joint may form a press-fit or friction-fit engagement to secure the insert 50 to the spacer 12 or the joint may be further secured, for example, with adhesive, pins 78, or the like.

The insert 50 is coupled to the spacer 12 such that at least a portion of the insert 50 is received in the cutout 24 in the spacer 12. The spacer 12 and the insert 50 may be coupled, removably coupled, connected, or attached together in any suitable manner known in the art. The spacer 12 and the insert 50 may also be coupled together through appropriate coupling means or fasteners. For example, the insert 50 and cutout 24 may be configured to provide male and female edges, which are the mechanical interfaces between the two pieces. Portions of the spacer 12 and the insert 50 may be assembled together using, alone or in combination, a friction fit, a dovetail assembly, dowel pins, hooks, staples, screws, adhesives, and the like, or any suitable fasteners known in the art, which can be used to permanently attach the spacer 12 and the insert 50 together.

In addition or in the alternative, the spacer 12 and the inserts 50 may be secured together with pins 78 which traverse at least a portion of the spacer 12 and/or the insert 50. For example, the arm 54 may include one or more openings 80 extending therethrough sized and configured to receive a portion of pin 78. Similarly, the corresponding portion of the spacer 12 may include one or more openings 80 extending therethrough sized and configured to receive the remainder of pin 78 to secure the arm 54 to the spacer 12. These openings 80 may or may not be threaded. The pins 78 may pass through holes 80, for example, in a substantially perpendicular manner relative to a horizontal plane to secure the joint between the insert 50 and the spacer 12. For example, the pins 78 may be oriented substantially perpendicular relative to the superior and/or inferior surfaces 42, 44 of the spacer 12. The pins 78 may be in the form of dowels or may be fully or partially threaded. The pins 78 may be formed from a biocompatible material, such as titanium, or the pins 78 may be formed from tantalum, for example, to enable radiographic visualization.

The head portion 52 of the insert 50 may include an upper surface 62 and a lower surface 64 depending on the orientation of the insert 50. For example, the two inserts 50 depicted in FIG. 1D are identical except the inserts 50 are oriented in opposite directions to fit the respective cutouts 24 in the spacer 12. The first insert 50a is oriented such that the upper surface 62 is configured to mate with a portion of the superior surface 42 of the spacer 12 and the lower surface 64 is configured to mate with a portion of the inferior surface 44 of the spacer. Conversely, the second insert 50b is oriented such that the lower surface 64 is configured to mate with a portion of the superior surface 42 of the spacer 12 and the upper surface 62 is configured to mate with a portion of the inferior surface 44 of the spacer.

The upper surface 62 and/or lower surface 64 of the head portion 52 of the insert 50 may extend a distance beyond the superior surface 42, the inferior surface 44, or both surfaces 42, 44 of the spacer 12. In particular, a portion of the head portion 52 of the insert 50 may extend above or below the superior and inferior surfaces 42, 44 of the spacer 12. For example, the lower surface 64 of the first insert 50a may extend beyond the inferior surface 44 and the lower surface 64 of the second insert 50b may extend beyond the superior surface 42 of the spacer 12.

The projection of the lower surfaces 64 of the first and second inserts 50a, 50b may be in the form of an eyebrow 60. The eyebrows 60 may fully capture the bone screws 30 while still allowing for the screw 30 to reside about, below, or above the base plane of the superior and inferior surfaces 42, 44. For example, a front surface 65 of the insert 12 may include at least one eyebrow 60 where the eyebrow 60 projects past the superior surface 42, the inferior surface 44, or both surfaces 42, 44 of the spacer 12. The eyebrow 60 may include a rounded portion. The eyebrow 60 may include a smooth surface or a roughened surface. As shown in FIG. 1B, the eyebrow 60 may be comprised of a smooth and curved surface. A lateral portion of the eyebrow 60 may further include one or more torsional stabilizers 70 configured to prevent or minimize torsional motion of the implant 1 once implanted. The torsional stabilizers 70 may act as extensions or fins, which may serve as knife edges to further purchase into the bone of the adjacent vertebrae or serve as a stop to abut anterior aspects of the adjacent vertebrae. The torsional stabilizer 70 may include a spiked or pointed projection or extension configured to engage adjacent vertebrae. In particular, the torsional stabilizer 70 may have a width substantially the same or less than a width of the eyebrow 60.

A portion of each of the upper surfaces 62 of the inserts 50 may also include an additional torsional stabilizer 70, for example, positioned opposite to the eyebrows 60. The torsional stabilizer 70 on the upper surfaces 62 may be the same or different than the torsional stabilizer 70 extending from the eyebrows 60. The upper surfaces 62 of the inserts 50 may complete a surface of the superior and inferior surfaces 42, 44 of the spacer 12 to enhance anchoring of the spacer 12. As shown in FIG. 1D, the spacer 12 may include a notch 23 in the cutout 24 in the superior and/or inferior surfaces 42, 44 of the spacer 12. The extension of the upper surface 62 including the torsional stabilizer 70 may fit in this notch 23 to form a continuous and contiguous superior and/or inferior surface for the implant 1. The notch 23 may be uniform in shape and dimension or non-uniform. In particular, the notch 23 may have a partial rectangular cross-section or may be any suitable shape to compliment the upper surface 62 of the insert 50 and complete the superior and/or inferior surfaces 42, 44 of the spacer 12.

Each insert 50 includes a screw hole or fastener aperture 34 sized and dimensioned to receive a fastener, such as screw 30. The screws 30 may be any suitable screws known in the art including fixed or variable angle. The screw hole 34 is configured to receive the screw 30 at a given angle. For example, the screw holes 34 for receiving the screw 30 may traverse the front surface 65 of the insert 50 at an angle divergent to a horizontal plane in order to secure the implant 1 to one of the adjacent vertebrae. Thus, in the case of implant 1 having two inserts 50 as shown in FIG. 1A, the screws 30 enter the screw holes 34 at specified angles to enter each of the adjacent vertebrae at the optimal locations. In particular, the screws 30 may be inserted at an angle for maximum screw purchase into the superior and inferior vertebral bodies.

The intervertebral implant 1 may be positioned in the spine after the disc portion between the two vertebral bodies is exposed and removed, for example, using rongeurs or other suitable instruments. The posterior and lateral walls of the annulus are generally preserved to provide peripheral support for the implant 1 and graft materials. A trial device attached to a trial holder may then be inserted into the disc space to determine size of the implant 1. This procedure is generally conducted using fluoroscopy and tactile feel. The implant 1 may be available in various heights and geometric options to fit the anatomical needs of a wide variety of patients. After the appropriate sized implant 1 is selected and attached to an implant holder and drill guide (not shown), the implant 1 may be inserted into the disc space. Before or after the implant 1 is positioned within the disc space, supplemental graft material can be used to enhance fusion. The implant 1 may be implanted in the vertebral space using an anterior, posterior, lateral, anterolateral, oblique, and/or transforaminal approach. The implant 1 shown in FIG. 1A may be particularly suitable for an anterior cervical procedure. The implant 1 may be in the form of a stand-alone fusion device to provide structural stability and a low or zero profile design. The implant 1 is preferably assembled before insertion into the disc space.

Once the implant 1 is positioned inside the disc space, an awl or any similar type of instrument, for example, can be used to drill through the screw hole and break the cortex of the adjacent vertebral body. The surgeon performing this procedure may then use a depth gauge to determine the screw length. Once the appropriate screw length is determined, screws 30 may be inserted using a self-retaining screwdriver, for example. Any suitable type of screw 30 may be selected by one of ordinary skill in the art. For example, the screws 30 may include fixed or variable angle screws of any suitable size with appropriate thread spacing, thread pitch, head design, length, and the like.

Once inserted, the screws 30 may be secured with an anti-back out prevention or locking mechanism 20. The locking mechanism 20 may be in the form of one or more blocking screw 32 to capture the sides of the inserted screws to prevent screw back out. As depicted in FIG. 1B, the locking mechanism 20 may be disposed on the spacer 12 for preventing back out of the screws 30. For example, a cam-style blocking mechanism may be used with screws 30 that capture the fixation device screws 30 once they are inserted fully into the inserts 50. The insert 50 may include a cutout 56 in the outer periphery of the head portion 52 configured such that the locking mechanism 20 may block or unblock the head of the screw 30. As shown, the anti-back out mechanism 20 may include a single set screw 32 that retains the screws 30 with the implant 1, although any suitable anti-back out mechanism 20 may be selected by one of ordinary skill in the art.

Figure 2A:
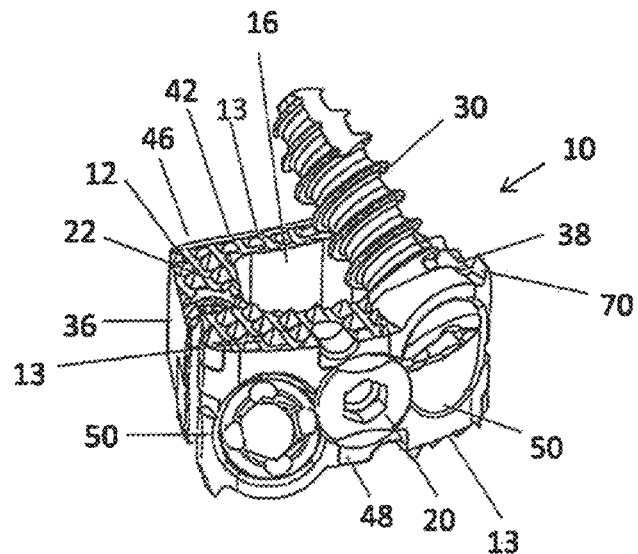
FIG. 2A shows a perspective view of an alternative embodiment of an interbody fusion device with inserts.
Figure 2B:
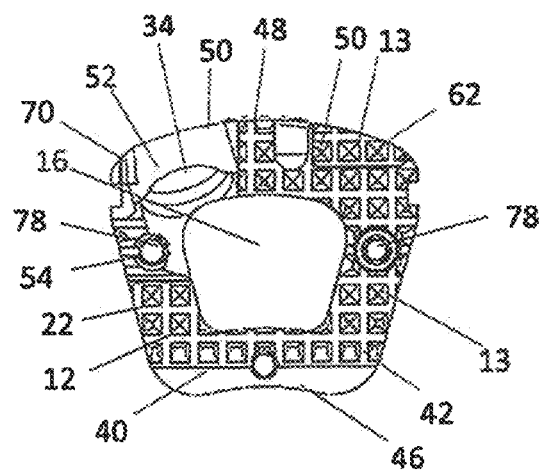
FIG. 2B is a top view of the embodiment shown in FIG. 2A.
Figure 2C:
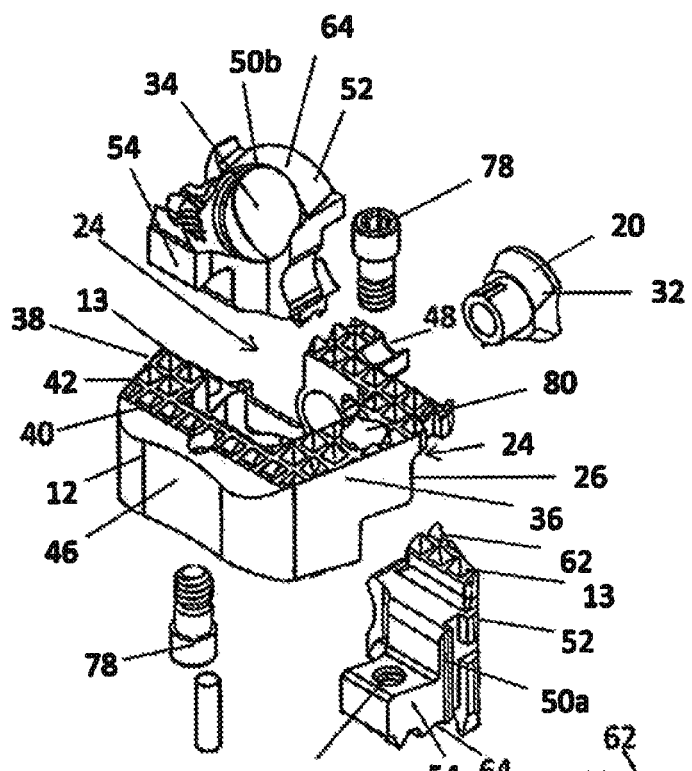
FIG. 2C is an exploded view of the embodiment shown in FIG. 2A.
Figure 2D:
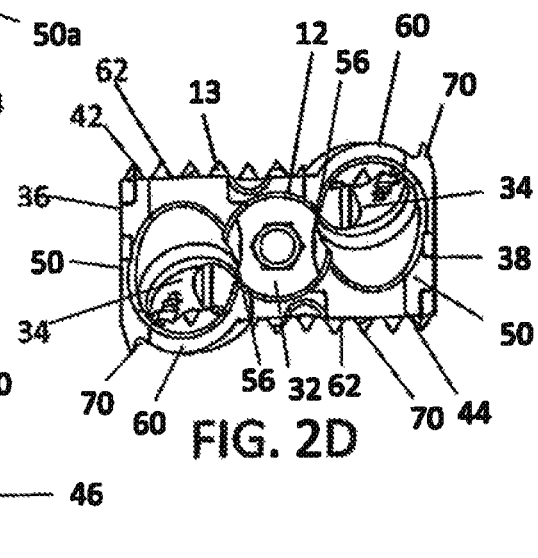
FIG. 2D is a front view of the embodiment shown in FIG. 2A.
Figure 2E:
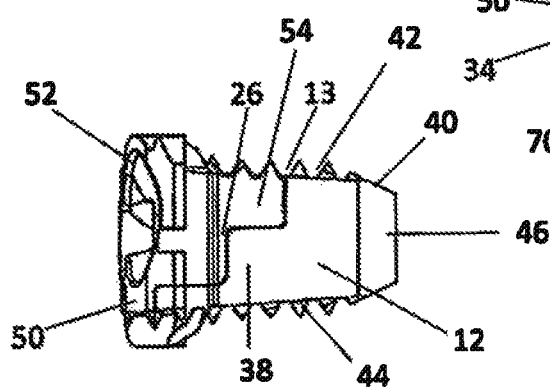
FIG. 2E is a lateral view of the embodiment shown in FIG. 2A.
Figure 3A:
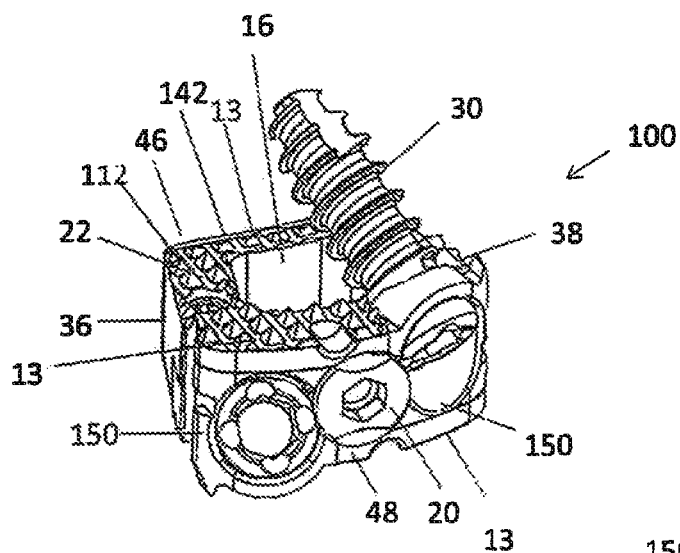
FIG. 3A is a perspective view of a third embodiment including a spacer with recessed inserts.
Figure 3B:
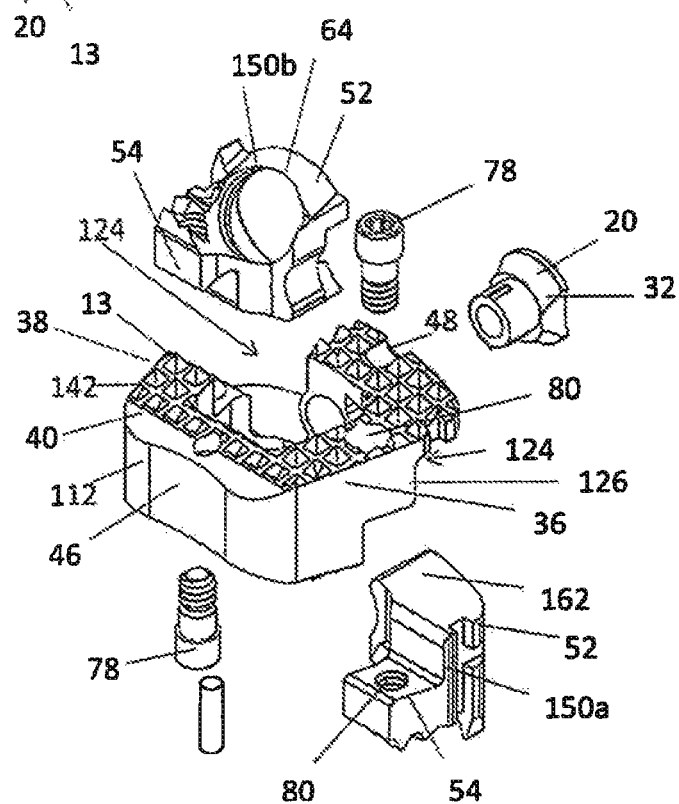
FIG. 3B shows an exploded view of the embodiment shown in FIG. 3A.
Figure 3C:
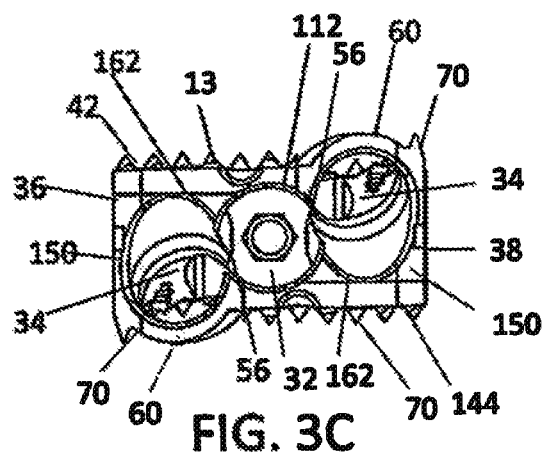
FIG. 3C shows a front view of the embodiment shown in FIG. 3A.
Figure 3D:
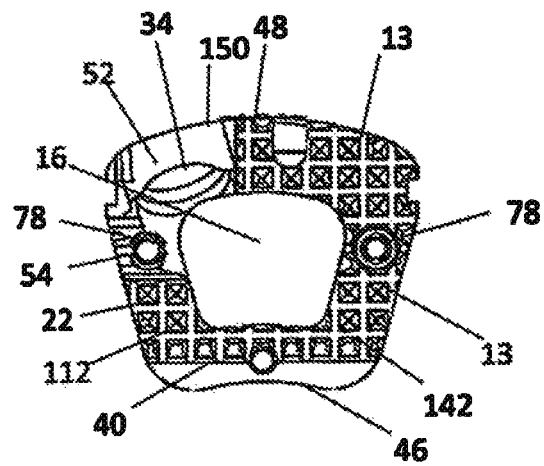
FIG. 3D is a top view of the embodiment shown in FIG. 3A.
Figure 3E:
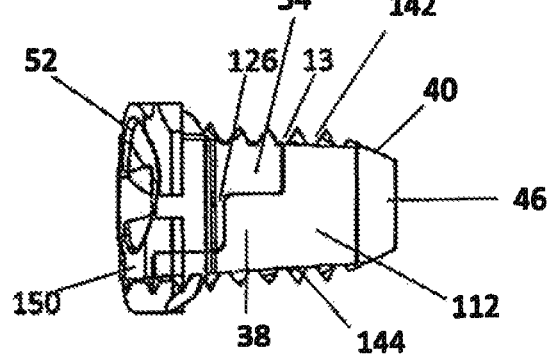
FIG. 3E is a lateral view of the embodiment shown in FIG. 3A.

FIGS. 2A-2E show alternative views of a second embodiment of an implant 10. In general, most of the structure of implant 10 is similar or comparable to the structure of implant 1. In this particular embodiment, the torsional stabilizers 70 on the upper surfaces 62 are replaced with a plurality of protrusions 13 or teeth. As shown in FIG. 2B, a portion of the upper surfaces 62 of the inserts 50a, 50b may include an extension with a plurality of protrusions 13 or teeth designed to extend the contact areas 22 of the superior and/or inferior surfaces 42, 44 of the spacer 12. The protrusions 13 on the upper surfaces 62 of the inserts 50a, 50b may complete a surface of the superior and inferior surfaces 42, 44 of the spacer 12 to enhance anchoring of the spacer 12. As shown in FIG. 2C, the spacer 12 may include the notch 23 in the cutout 24 in the superior and/or inferior surfaces 42, 44 of the spacer 12. The notch 23 may be uniform in shape and dimension or non-uniform. In particular, the notch 23 may have a partial rectangular cross-section. The extension of the upper surface 62 including the plurality of protrusions 13 may fit in this notch 23 to form a continuous and contiguous superior and/or inferior surface for the implant 10. The plurality of protrusions 13 may be the same or different than the protrusions 13 provided on the remainder of the spacer 12.

According to a third embodiment, FIGS. 3A-3E show alternative views an implant 100. In general, most of the structure of implant 100 is similar or comparable to the structure of implant 1. In this particular embodiment, different inserts 150 are provided. In particular, the upper surfaces 162 of the inserts 150a, 150b do not include a plurality of protrusions and are instead smooth. These smooth upper surfaces 162 do not complete the superior and inferior surfaces 142, 144 of the spacer 112. Instead, the smooth upper surfaces 162 are recessed and mated beneath the superior and inferior surfaces 142, 144 of the spacer 112. In addition, the cutouts 124 are modified from those shown in implant 1. For example, the superior and inferior surfaces 142, 144 of the spacer 112 are not notched to receive a portion of the insert 150, but instead extend to the proximal end 48 of the spacer. As is evident in FIG. 3B, a portion of the stepped projection 126 on the spacer 112 is extended to be contiguous and flush with the proximal end 48 of the spacer 112.

According to a fourth embodiment, FIGS. 4A-4E show an implant 200, which may be particularly suitable for an anterior lumbar procedure. In general, most of the structure of implant 200 is similar or comparable to the structure of implant 1. In this particular embodiment, three different inserts 250 provide the fastener apertures 234.

Figure 4A:
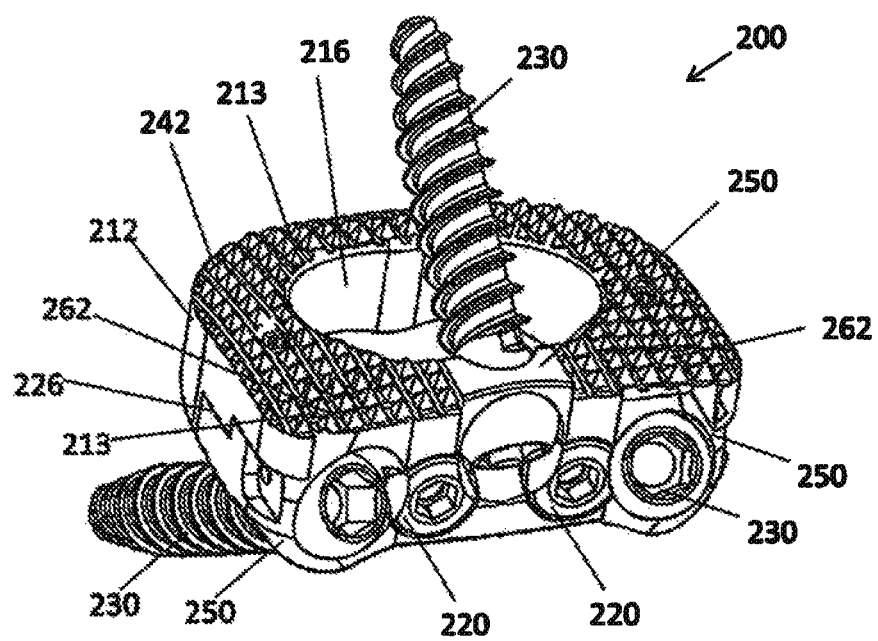
FIG. 4A shows a perspective view of a fourth embodiment of an implant suitable for lumbar interbody fusion including a spacer with three inserts.
Figure 4B:
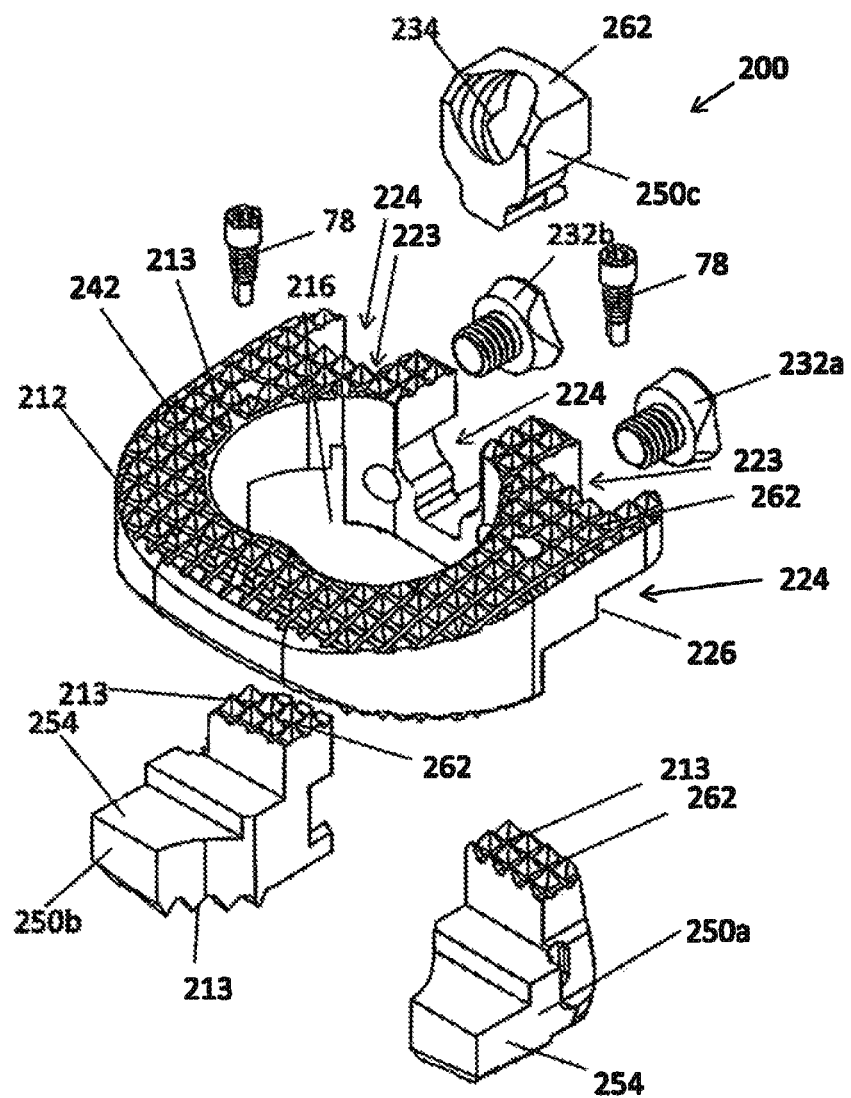
FIG. 4B is an exploded view of the embodiment shown in FIG. 4A.
Figure 4C:
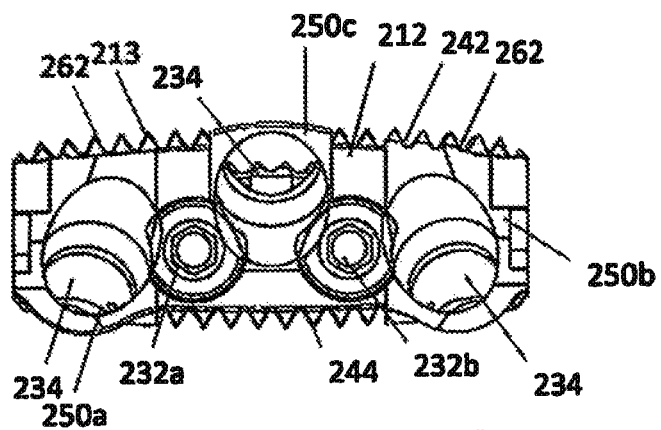
FIG. 4C is a front view of the embodiment shown in FIG. 4A.
Figure 4D:
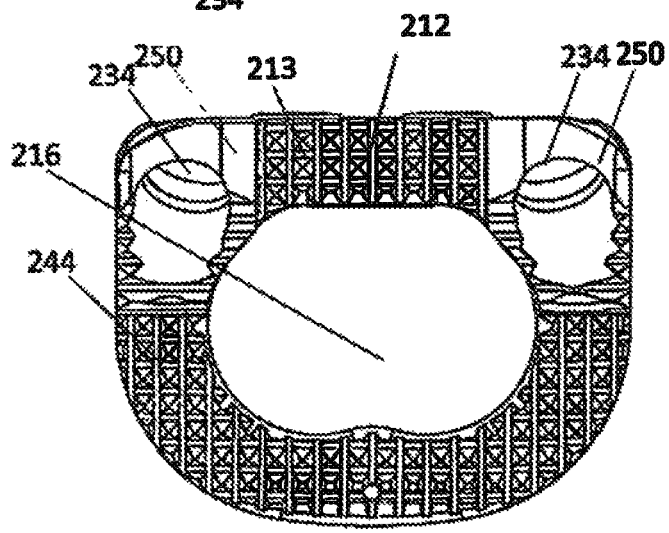
FIG. 4D is a bottom view of the embodiment shown in FIG. 4A.
Figure 4E:
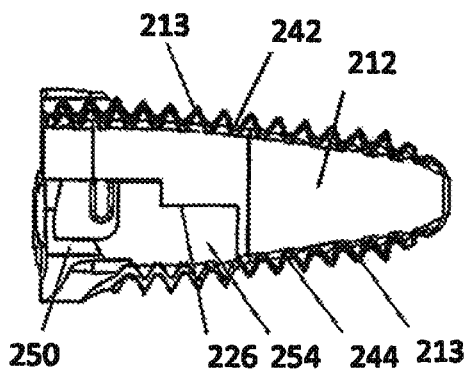
FIG. 4E is a lateral view of the embodiment shown in FIG. 4A.

A shown in FIG. 4B, a first insert 250a is identical to a second insert 250b except as mirror images of one another to fit the respective cutouts 224 in the spacer 212. The first and second inserts 250a, 250b each define a fastener aperture 234. The first and second inserts 250a, 250b are each configured to allow a bone screw 230 to engage superior or inferior vertebra. Similar to implant 1, the spacer 212 may include one or more cutouts 224 sized and configured to retain the inserts 250. The cutouts 224 may further define a stepped projection 226 configured to mate with the arm 254 of the insert 250. The arm 254 may also be stepped and configured to mate with corresponding stepped projections 226 on the spacer 212. A portion of the insert 250 may be stepped with a male projection to mate with a stepped female configuration of the spacer 212. The arm 254 may include a series of offset planar surfaces, for example, having a rise and a run, to form the stepped profile. The cutouts 224 may be in fluid communication with the opening 216 extending from the superior surface 242 to the inferior surface 244 of the spacer 212.

In addition, the spacer 212 may include one or more notches 223 in the cutout 224 in the superior surface 242 and/or inferior surface 244 of the spacer 212. The extension of the upper surface 262 of the insert 250 including the plurality of protrusions 213 may fit in the respective notch 223 to form a continuous and contiguous superior surface for the implant 200. A third insert 250c is provided between the first and second inserts 250a, 250b. The third insert 250c is different from the first and second inserts 250a, 250b and allows a bone screw 230 to engage a superior vertebra. Although the third insert 250c is depicted with a smooth upper surface 262, the third insert 250c may also include projections 213, torsional stabilizers, or the like.

The fastener apertures 234 may be configured such that the locking mechanism 220 may block or unblock the heads of the screws 230 in the respective fastener apertures 234. As shown, the anti-back out mechanism 220 may include a first set screw 232a that is configured to block a portion of the screw 230 in the first insert 250a and the screw 230 in the third insert 250c and a second set screw 232b that is configured to block a portion of the screw 230 in the second insert 250b and the screw 230 in the third insert 250c.

FIGS. 5A-5F show a fifth embodiment of an implant 300. In general, most of the structure of implant 300 is similar or comparable to the structure of implant 1. In this particular embodiment, two different inserts 350 provide the fastener apertures 334. In this case, modified arms 354 are at least partially received in at least one recess 318 in the spacer 312 to join the insert 350 to the spacer 312. The recess 318 may extend a set depth into the spacer 312 from the opening 316. The recess 318 may be in fluid communication with the opening 316. The recess 318 may be formed in the lateral portions and/or the distal portion of the opening 316. The recess 318 may be positioned substantially medially between and substantially parallel to the superior and/or inferior surfaces 342, 344 of the spacer 312. The recess 318 may be sized and dimensioned to retain at least a portion of the arm 354 of the insert 350.

Figure 5A:
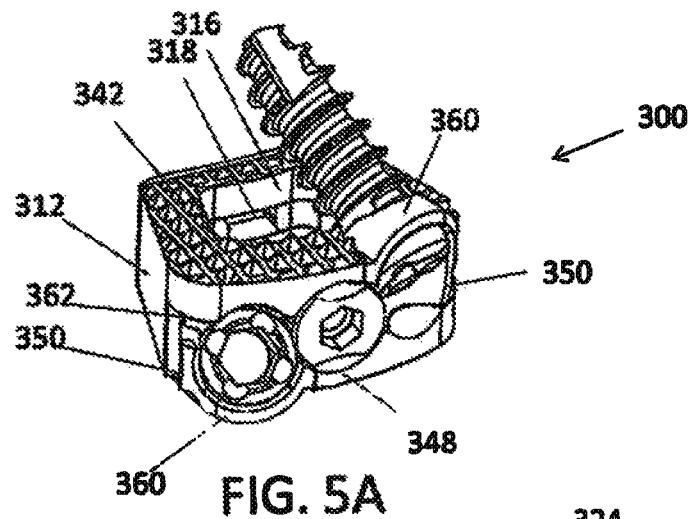
FIG. 5A is a perspective view of a fifth embodiment including inserts with head and arm portions.
Figure 5B:
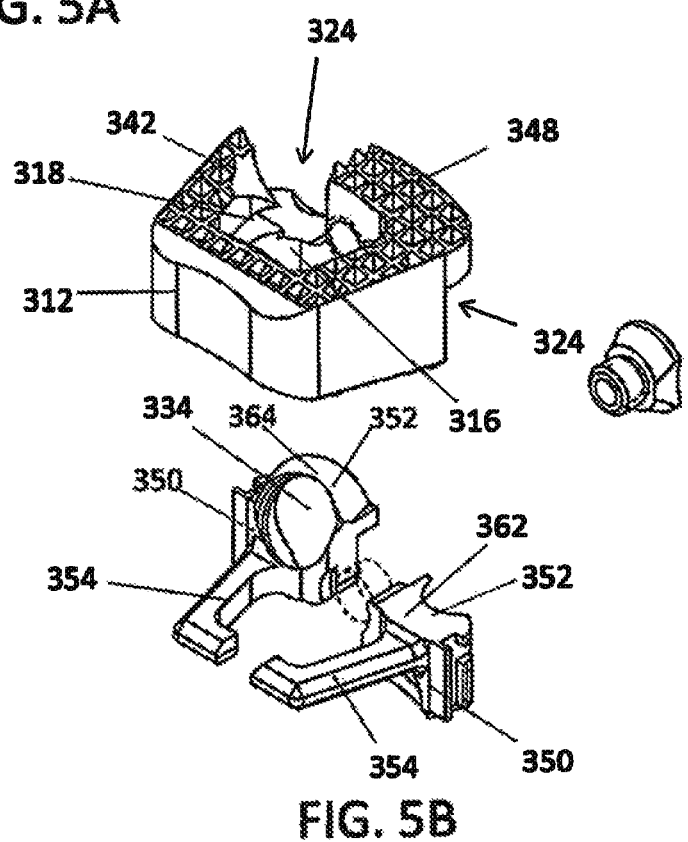
FIG. 5B shows an exploded view of the embodiment shown in FIG. 5A.
Figure 5C:
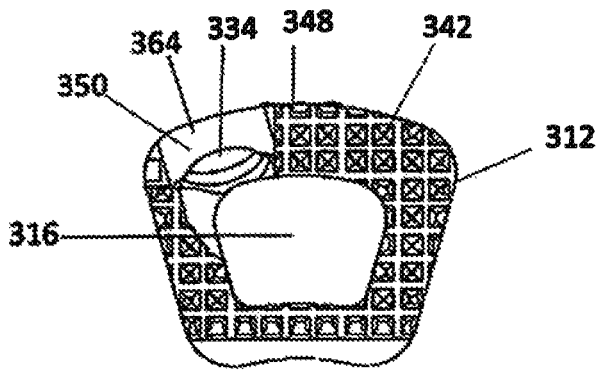
FIG. 5C shows a top view of the embodiment shown in FIG. 5A.
Figure 5D:
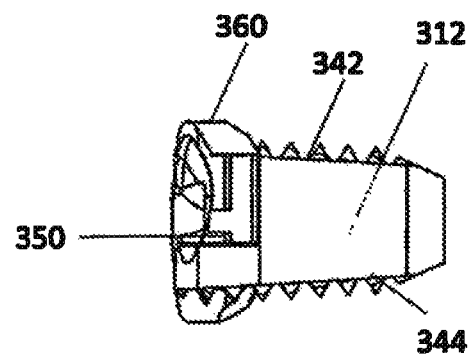
FIG. 5D is a lateral view of the embodiment shown in FIG. 5A.
Figure 5E:
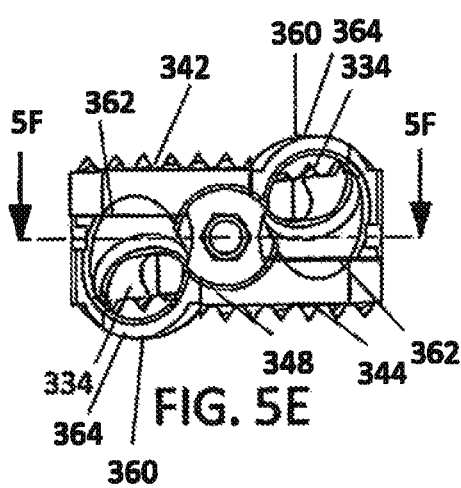
FIG. 5E is a front view of the embodiment shown in FIG. 5A.
Figure 5F:
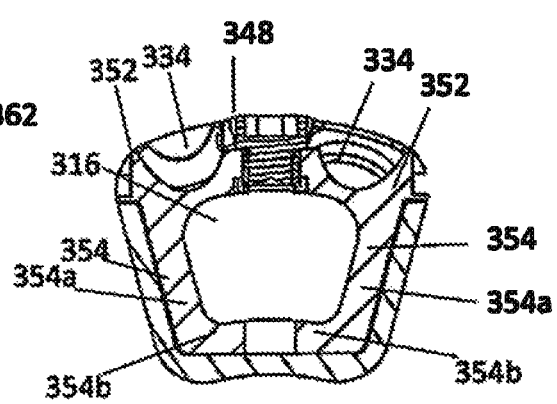
FIG. 5F is a cross-sectional view as designated in FIG. 5E.
Figure 6A:
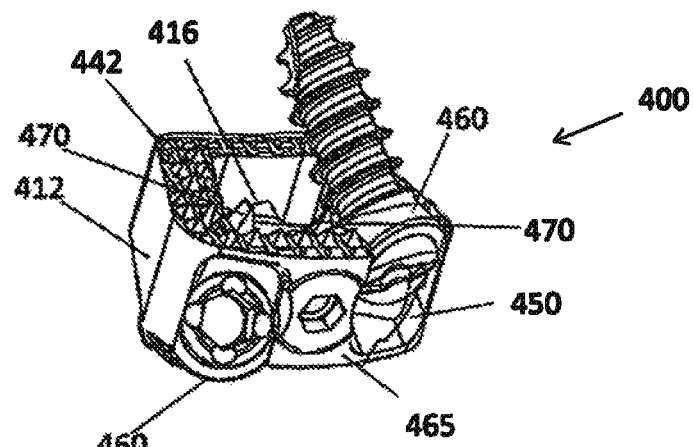
FIG. 6A is a perspective view of a sixth embodiment including a single insert recessed behind the front portion of the spacer.
Figure 6B:
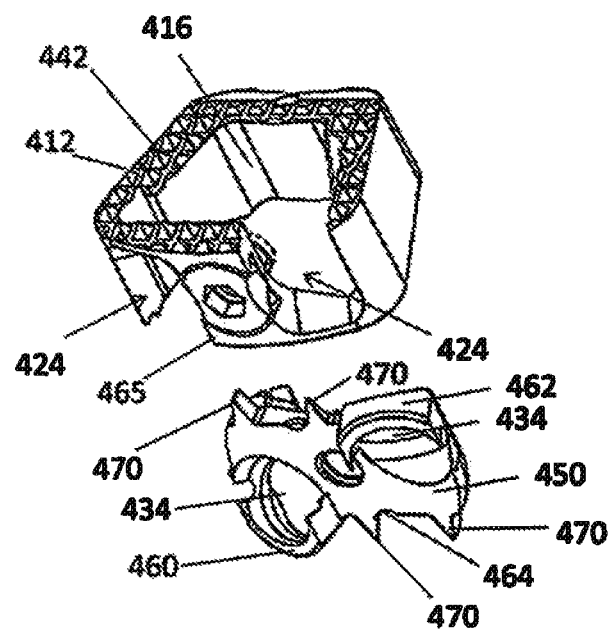
FIG. 6B shows an exploded view of the embodiment shown in FIG. 6A.
Figure 6C:
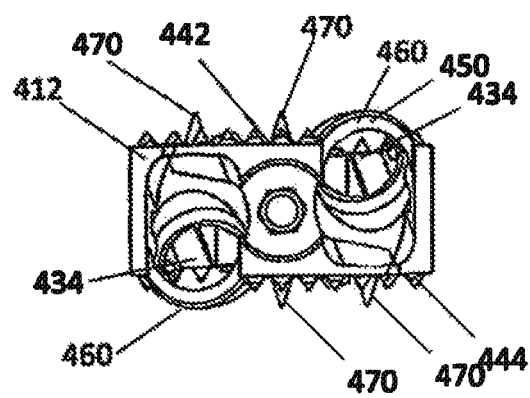
FIG. 6C is a front view of the embodiment shown in FIG. 6A.
Figure 6D:
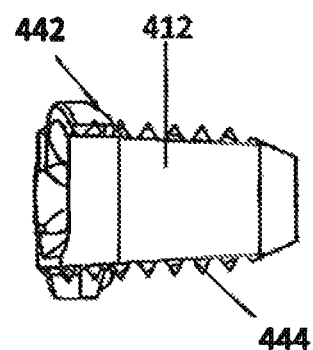
FIG. 6D is a lateral view of the embodiment shown in FIG. 6A.
Figure 6E:
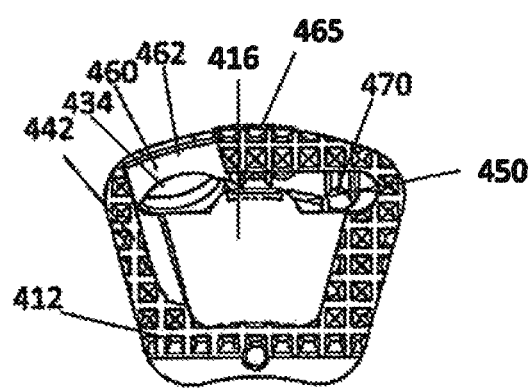
FIG. 6E is a top view of the embodiment shown in FIG. 6A.

The two inserts 350 depicted in FIG. 5B are identical except are oriented in opposite directions to fit the respective cutouts 324 in the spacer 312. The insert 350 may include head portion 352 and arm 354 extending therefrom. The arm 354 may extend posteriorly away from the head portion 352 and toward the distal end 346 of the spacer 312 when attached thereto. The arm 354 may be angled relative to the head portion 352 such that the arm 354 is oriented in a medial direction, for example, to mimic the shape of the spacer 312.

Each arm 354 of the insert 350 may include a first arm portion 354a and a second arm portion 354b. The first arm portion 354a may connect the head portion 352 of the insert 350 to the second arm portion 354b. The second arm portion 354 may be angled relative to the first arm portion 354a. The first arm portion 354a may engage the lateral portions of the recess 318 in the spacer 312, and the second arm portion 354b may engage the distal portion of the recess 318 in the spacer 312. The upper surface 362 of the insert 350 including the head portion 352, the first arm portion 354a, and the second arm portion 354b may be a continuous and contiguous coplanar surface. In the alternative, the arm 354 may be recessed beneath the upper surface 362 of the head portion 352. The arms 354 of the inserts 350 may join the spacer 312 via a press-fit or friction-fit engagement to secure the insert 350 to the spacer 312 or the joint may be further secured, for example, with adhesive, pins, or the like.

Similar to implant 1, the lower surface 364 of the head portion 352 of the insert 350 may extend a distance beyond the superior surface 342, the inferior surface 344, or both surfaces 342, 344 of the spacer 312. For example, the lower surface 364 of the first insert 350a may extend beyond the inferior surface 344 and the lower surface 364 of the second insert 350b may extend beyond the superior surface 342 of the spacer 312. The projection of the lower surfaces 364 of the first and second inserts 350a, 350b may be in the form of eyebrows 360. In this embodiment, the eyebrow 360 includes a substantially smooth and curved surface. In the embodiment shown, no torsional stabilizers are present, but one or more torsional stabilizers may be added if desired.

Similar to implant 100, the upper surfaces 362 of the inserts 350a, 350b do not include a plurality of protrusions and are instead smooth. These smooth upper surfaces 362 do not complete the superior and inferior surfaces 342, 344 of the spacer 312. Instead, the smooth upper surfaces 362 are recessed and mated beneath the superior and inferior surfaces 342, 344 of the spacer 312. In addition, the cutouts 324 are different from those shown in implant 1. For example, the superior and inferior surfaces 342, 344 of the spacer 312 are not notched to receive a portion of the insert 350, but extend to the proximal end 348 of the spacer.

FIGS. 6A-6E show a sixth embodiment of an implant 400 including a single member 450 recessed behind the front portion of the spacer 412. In general, most of the structure of implant 400 is similar or comparable to the structure of implant 1. Unlike the individual inserts 50 provided for each fastener aperture 34 in implant 1, in this particular embodiment, a single member 450 provides all of the fastener apertures 434.

In this embodiment, the single member 450 provides two fastener apertures 434 to secure fasteners in both the superior and inferior vertebrae. This member 450 may be provided with or without arms. The member 450 may be recessed in the spacer 412 and positioned posterior to the front surface 465 of the spacer 412. In particular, the member 450 may be positioned within the opening 416 such that a first portion of the member 450 is received in a first cutout 424 in the spacer 412 and a second portion of the member 450 is received a second cutout 424 in the spacer 412. The member 450 may be curved and contoured to follow a proximal portion of the spacer 412.

Similar to implant 1, the upper and/or lower surfaces 462, 464 of the member 450 may extend a distance beyond the superior surface 442, the inferior surface 444, or both surfaces 442, 444 of the spacer 412. For example, a portion of the upper surface 462 of the member 450 may extend above the superior surface 442 and a portion of the lower surface 464 may extend below the inferior surface 444 of the spacer 412. The projections of the upper and lower surfaces 462, 464 of the single member 450 may be in the form of eyebrows 460. In this embodiment, the eyebrows 460 include a substantially smooth and curved surface. In the embodiment shown, torsional stabilizers 470 are provided opposite to the eyebrows 460 and are also provided substantially medially on the member 450 projecting superiorly and inferiorly from both the upper and lower surfaces 462, 464, respectively. The torsional stabilizers 470 may include a spiked or pointed projection or extension configured to engage adjacent vertebrae.

According to a seventh embodiment, FIGS. 7A-7E depict an implant 500 with a different type of insert 550. In general, most of the structure of implant 500 is similar or comparable to the structure of implant 1. Unlike the inserts 50 provided with arm 54 in implant 1, in this particular embodiment, the insert 550, which provides the fastener aperture 534, does not contain an arm and is directly recessed into at least one slot 518 in the spacer 512.

Figure 7A:
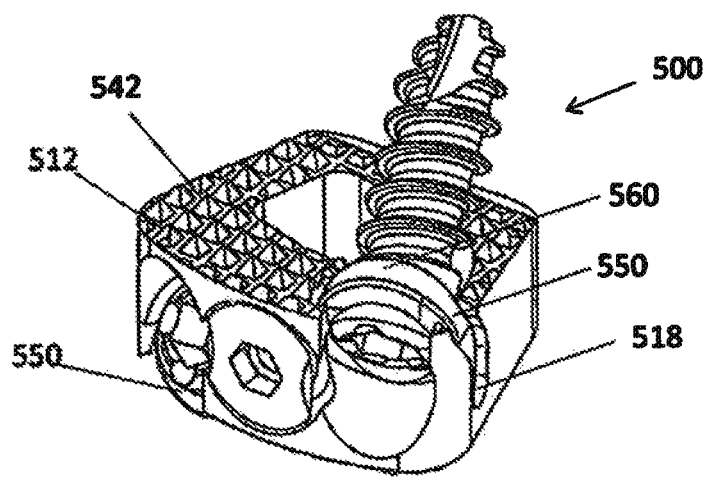
FIG. 7A shows a perspective view of a seventh embodiment with alternative inserts.
Figure 7B:
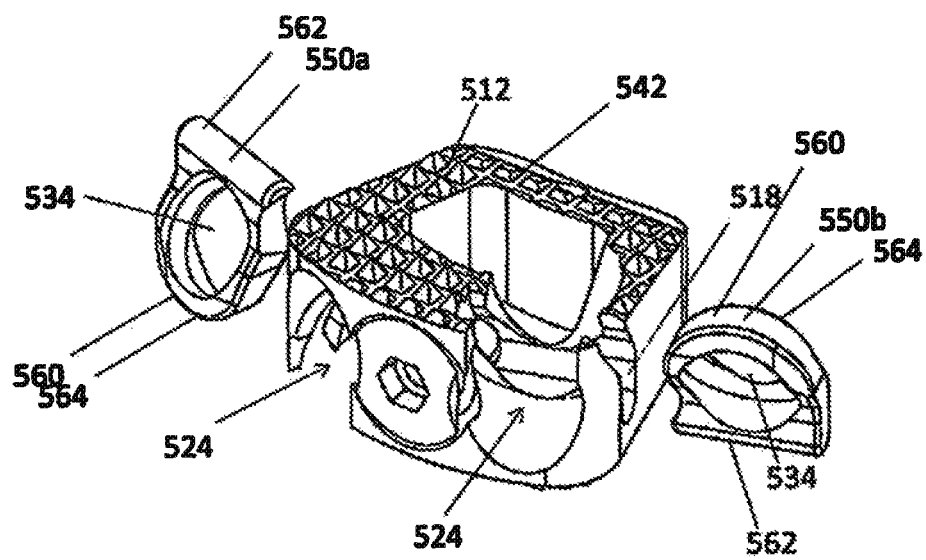
FIG. 7B shows an exploded view of the embodiment shown in FIG. 7A.
Figure 7C:
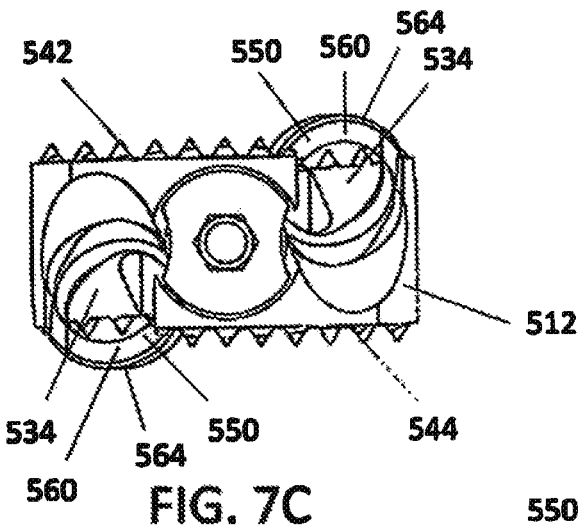
FIG. 7C is a front view of the embodiment shown in FIG. 7A.
Figure 7D:
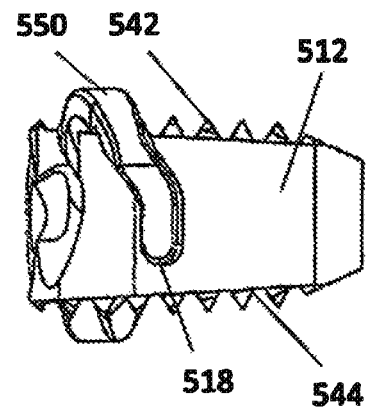
FIG. 7D is a lateral view of the embodiment shown in FIG. 7A.

The two inserts 550 depicted in FIG. 7B are identical except are oriented in opposite directions to fit the respective cutouts 524 in the spacer 512. The insert 550 may be curved or may contain one or more angled transitions. At least a portion of the inserts 550 may join the spacer 512 via a press-fit or friction-fit engagement to secure the insert 550 to the spacer 512 or the joint may be further secured, for example, with adhesive, pins, or the like.

In this embodiment, the inserts 550 are at least partially received in at least one slot 518 in the spacer 512 to join the insert 550 to the spacer 512. The slot 518 may extend a set depth into the spacer 512 from the cutout 524. For example, the slot 518 may be formed in an inferior or superior portion of the cutout 524 and may be in fluid communication with the cutout 524. The slot 518 may include more than one portion including an angled portion, for example. The angled portion may connect the eyebrow 560 to a planar portion. The planar portion may be positioned substantially perpendicular to the superior and/or inferior surfaces 542, 544 of the spacer 12. The slot 518 may be sized and dimensioned in any suitable configuration to retain at least a portion of the insert 550. For example, the upper surface 562 of the insert 550 may contact and fit within the slot 518. The upper surfaces 562 of the inserts 550 may be substantially smooth or may be textured. The upper surface 562 may also be curved or rounded as shown. These smooth upper surfaces 562 are recessed and mated beneath the superior and inferior surfaces 542, 544 of the spacer 512.

Figure 7E:
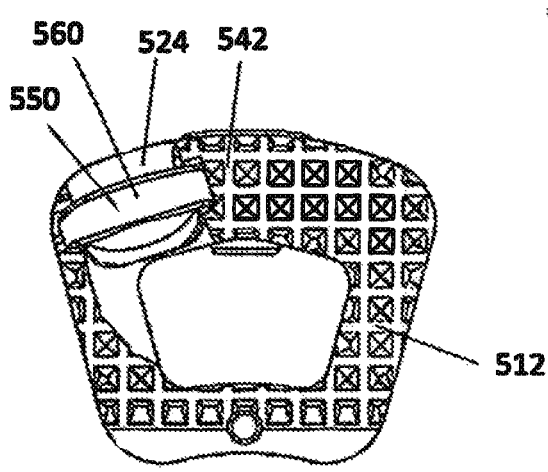
FIG. 7E is a top view of the embodiment shown in FIG. 7A.

In this embodiment, the depth of the insert 550 may be the same or smaller than the depth of the proximal portion of the spacer. In other words, the insert 550 does not need to fill the entire depth of the cutout 524. As shown in FIG. 7E, the insert 550 fills only a portion of the cutout 524. In this embodiment, the insert 550 is positioned substantially centrally in the cutout 524, but it is envisioned that the insert 550 may be positioned at any suitable location in the cutout 524.

Similar to implant 1, the lower surface 564 of the insert 550 may extend a distance beyond the superior surface 542, the inferior surface 544, or both surfaces 542, 544 of the spacer 512. For example, the lower surface 564 of the first insert 550a may extend below the inferior surface 544 and the lower surface 564 of the second insert 550b may extend above the superior surface 542 of the spacer 512. The projection of the lower surfaces 564 of the first and second inserts 550a, 550b may be in the form of an eyebrow 560. In this embodiment, the eyebrow 560 includes a substantially smooth and curved surface. In the embodiment shown, no torsional stabilizers are present, but one or more torsional stabilizers may be added if desired.

FIGS. 8A-8E provide an eighth embodiment of an implant 600 where the inserts 650 are in the form of rings. In general, most of the structure of implant 600 is similar or comparable to the structure of implant 1. In addition, this embodiment is similar to the implant 500 discussed above.

Figure 8A:
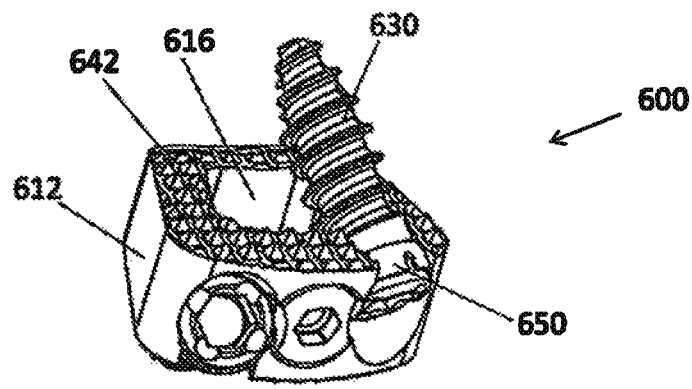
FIG. 8A provides a perspective view of an eight embodiment where the inserts are in the form of rings.
Figure 8B:
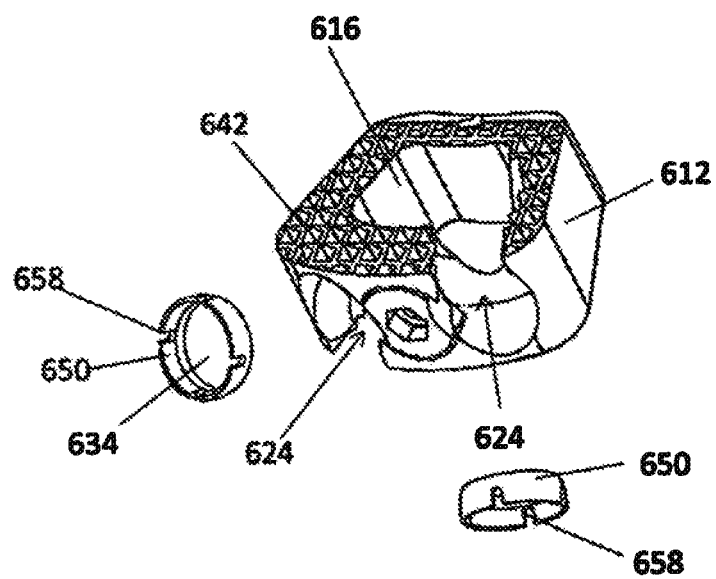
FIG. 8B shows an exploded view of the embodiment shown in FIG. 8A.
Figure 8C:
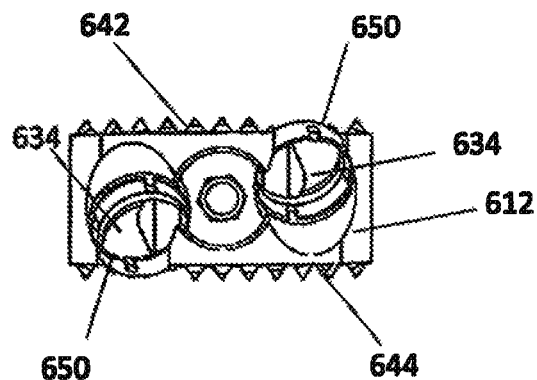
FIG. 8C is a front view of the embodiment shown in FIG. 8A.
Figure 8D:
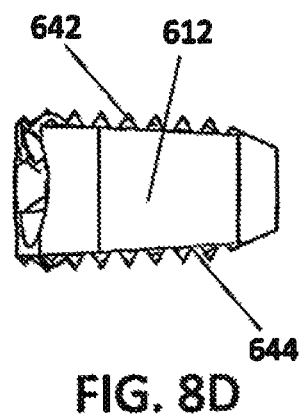
FIG. 8D is a lateral view of the embodiment shown in FIG. 8A.
Figure 8E:
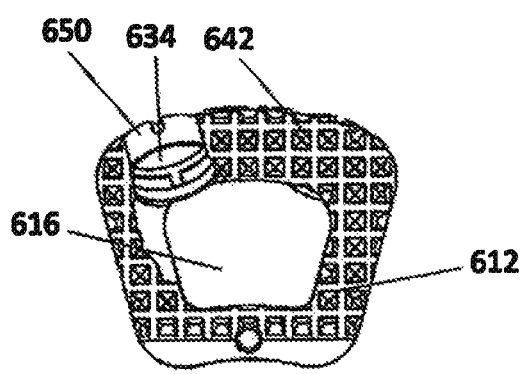
FIG. 8E is a top view of the embodiment shown in FIG. 8A.

In this embodiment, the insert 650 is in the form of a ring or cylinder. The ring insert 650 may be provided with one or more slits 658, for example, to allow the insert 650 to tightly mate with the cutout 624 through the spacer 612 and secure the insert 650 to the spacer 612. In particular, one or more slits 658 may be longitudinally positioned around a periphery of the ring-shaped insert 650. The slits 658 may be uniformly or non-uniformly positioned around the insert 650. As shown in FIG. 8B, the slits 658 may be positioned in 90° increments around the ring insert 650. For example, four slits 658 may be positioned around the periphery of the ring insert 650. The slits 658 may be oriented such that the open ends of the slits 658 face anteriorly.

The insert 650 may be received in a recess in the cutout 624 or may be positioned within the cutout 624. The cutouts 624 may be in fluid communication with the opening 616 extending from the superior surface 642 to the inferior surface 644 of the spacer 612. The insert 650 may be configured to at least partially define and reinforce the fastener aperture 634. At least a portion of the inserts 650 may join the spacer 612 via a press-fit or friction-fit engagement to secure the insert 650 to the spacer 612. The insert 650 may be further secured, for example, with adhesive or the like.

In this embodiment, the depth of the insert 650 may be the same or smaller than the depth of the proximal portion of the spacer. In other words, the insert 650 does not need to fill the entire depth of the cutout 624. In this embodiment, the insert 650 is positioned at an angle in the cutout 624 to accommodate the angles of the bone screws 630. It is envisioned that the insert 650 may be positioned at any suitable location in the cutout 624.

Figure 9A:
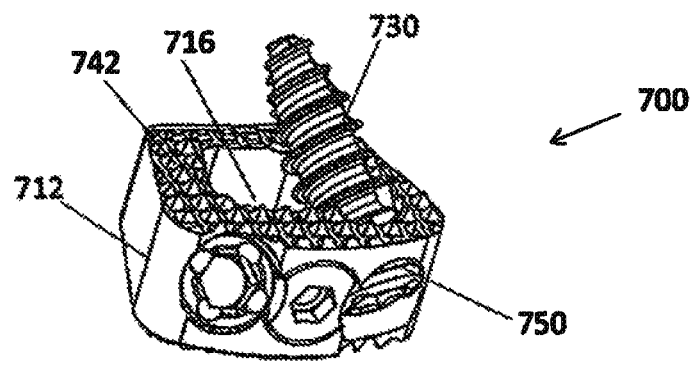
FIG. 9A is a perspective view of a ninth embodiment where the inserts have a c-shaped configuration.
Figure 9B:
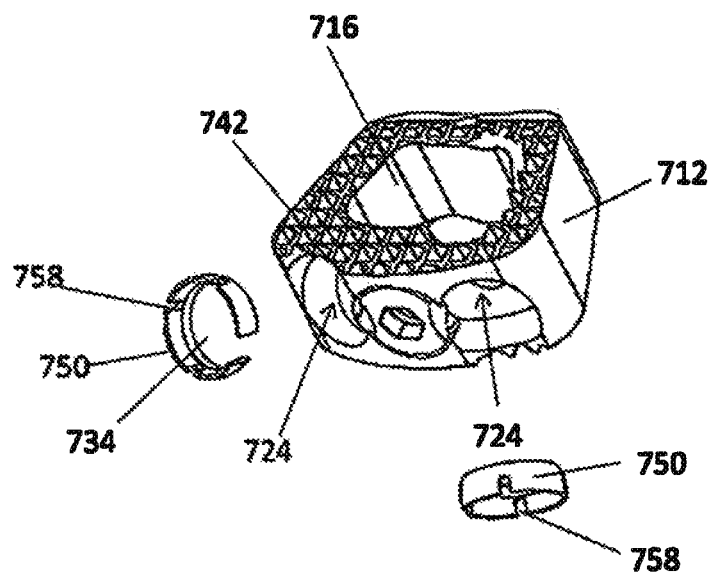
FIG. 9B shows an exploded view of the embodiment shown in FIG. 9A.
Figure 9C:
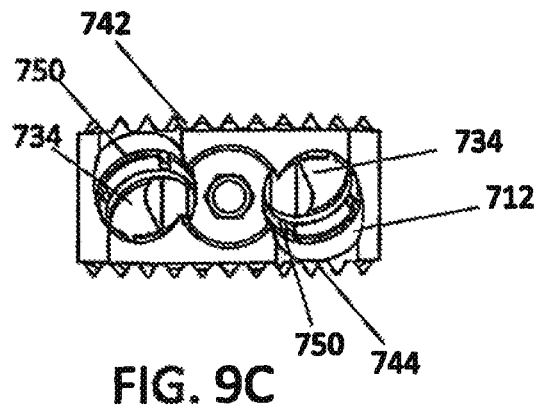
FIG. 9C is a front view of the embodiment shown in FIG. 9A.
Figure 9D:
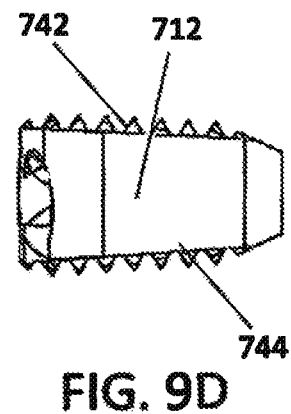
FIG. 9D is a lateral view of the embodiment shown in FIG. 9A.
Figure 9E:
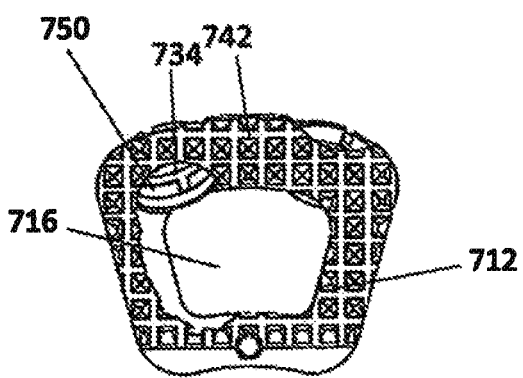
FIG. 9E is a top view of the embodiment shown in FIG. 9A.
Figure 11C:
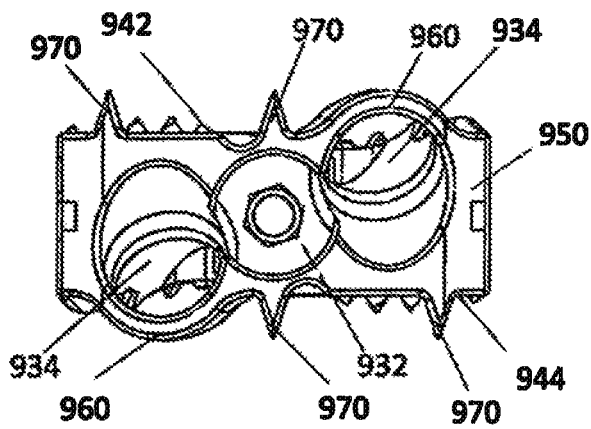
FIG. 11C is a front view of the embodiment shown in FIG. 11A.
Figure 11D:
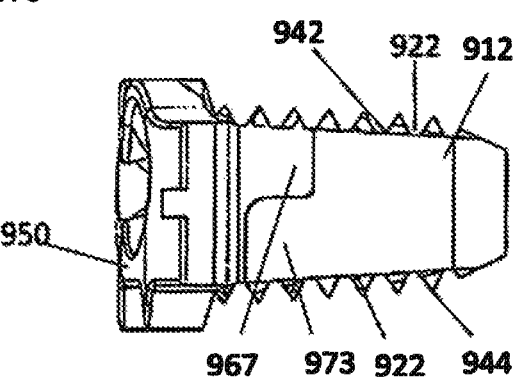
FIG. 11D is a lateral view of the embodiment shown in FIG. 11A.
Figure 11E:
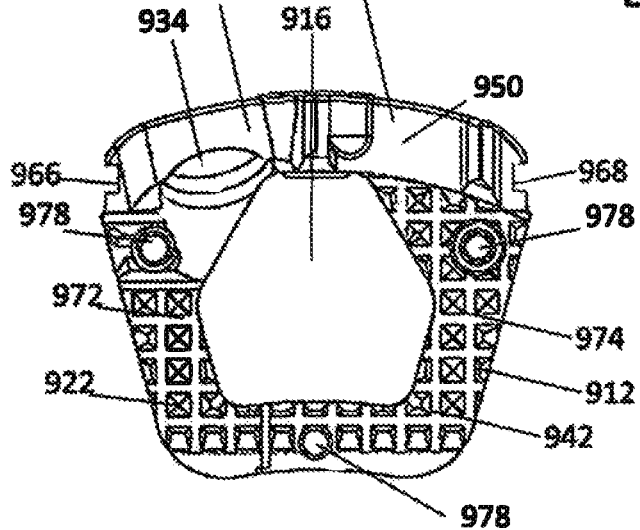
FIG. 11E is a top view of the embodiment shown in FIG. 11A.

FIGS. 9A-9E provide a ninth embodiment of an implant 700. In general, most of the structure of implant 700 is similar or comparable to the structure of implant 1. In addition, this embodiment is substantially the same as the implant 600 discussed above, and the discussion for implant 600 applies equally here. In this particular embodiment, the insert 750 has a c-shaped cross-section instead of being in the form of a ring. The c-shaped inserts 750 shown in FIG. 9B are the same except are oriented differently. The c-shaped inserts 750 are substantially the same as the ring inserts 650 except a gap separates the insert 750 to allow for further compression and/or expansion of the insert 750.

The c-shaped insert 750 may also be provided with one or more slits 758, for example, to allow the insert 750 to tightly mate with the cutout 724 through the spacer 712 and secure the insert 750 to the spacer 712. In particular, one or more slits 758 may be longitudinally positioned around a periphery of the c-shaped insert 750. The slits 758 may be uniformly or non-uniformly positioned around the insert 750. The slits 758 may also positioned in 90° increments around the c-shaped insert 750. For example, three slits 758 may be positioned around the periphery of the ring insert 750. The slits 758 may be oriented such that the open ends of the slits 758 face anteriorly.

The insert 750 may be received in a recess in the cutout 724 or may be positioned within the cutout 724. The cutouts 724 may be in fluid communication with the opening 716 extending from the superior surface 742 to the inferior surface 744 of the spacer 712. The insert 750 may be configured to at least partially define the fastener aperture 734. At least a portion of the inserts 750 may join the spacer 712 via a press-fit or friction-fit engagement to secure the insert 750 to the spacer 712. The insert 750 may also be secured, for example, with adhesive or the like. In this embodiment, the depth of the insert 750 may be the same or smaller than the depth of the proximal portion of the spacer. Similar to insert 650, the c-shaped insert 750 does not need to fill the entire depth of the cutout 724. In this embodiment, the insert 750 is positioned at an angle in the cutout 724 to accommodate the angles of the bone screws 730, but it is envisioned that the insert 750 may be positioned at any suitable location in the cutout 724 so long as the necessary reinforcement is provided to the fasteners.

According to a tenth embodiment, FIGS. 10A-10C provide an implant 800 with a member 850. In general, most of the structure of implant 800 is similar or comparable to the structure of implant 1. Unlike the individual inserts 50 provided for each fastener aperture 34 in implant 1, in this particular embodiment, a member 850 provides all of the fastener apertures 834. The member 850 may be in the form of a clamp or clip, which surrounds a proximal portion of the spacer 812.

In this embodiment, the member 850 provides two fastener apertures 834 to secure fasteners in both the superior and inferior vertebrae. This member 850 may be provided with or without arms. The member 850 may be positioned posterior to the front surface 865 of the spacer 812. In particular, the member 850 may be positioned to surround or envelop a portion of at least one lateral side 836, 838 and a portion of the superior and/or inferior surfaces 842, 844 of the spacer 812. The member 850 may be contoured, for example, to begin at one lateral side 836 wrap around a portion of the superior surface 842 to define one of the fastener apertures 834, wrap around the other lateral side 838, wrap under a portion of the inferior surface 844 to define the other fastener aperture 834, and terminate at the lateral side 836. The member 850 may begin and terminate at one lateral side 836, 838, for example, using one or more clamping features 882. The clamping features 882 may include prongs or springs which attach or secure the member 850 to the spacer 812. Although the member 850 is depicted as a single piece, it is envisioned that the clamping member 850 may be comprised of more than one part so long as the member 850 may clamp to the spacer 812 and provide the fastener apertures 834.

A portion of the upper and/or lower surfaces 862, 864 of the member 850 may extend a distance beyond the superior surface 842, the inferior surface 844, or both surfaces 842, 844 of the spacer 812. For example, a portion of the upper surface 862 may extend above the superior surface 842 and a portion of the lower surface 864 may extend below the inferior surface 844 of the spacer 812. The projections of the upper and lower surfaces 862, 864 of the single insert 850 may be in the form of eyebrows 860. In this embodiment, the eyebrows 860 include a substantially smooth and curved surface. In the embodiment shown, torsional stabilizers 870 are also provided substantially medially and laterally on the member 850 projecting superiorly and inferiorly from both the upper and lower surfaces 862, 864, respectively. The torsional stabilizers 870 may include a spiked or pointed projection or extension configured to engage adjacent vertebrae.

FIGS. 11A-11E provide an eleventh embodiment of an implant 900. In general, the structure of implant 900 is similar or comparable to the structure of implant 1. In this embodiment, the inserts 50 have been replaced with a member 950 and the spacer 912 includes multiple components.

The spacer 912 has a first spacer portion 972 and a second spacer portion 974. The first spacer portion 972 has a first end 972a and a second end 972b, and the second spacer portion 974 has a first end 974a and a second end 974b. The second end 972b of the first spacer portion 972 is coupled to the first end 974a of the second spacer portion 974. The first and second spacer portions 972, 974 form the superior surface 942 and the inferior surface 944 of the spacer 912. The superior surface 942 and the inferior surface 944 each have a contact area 922 configured to engage adjacent vertebrae. The first and second spacer portions 972, 974 and the member 950 join to form an opening 916 extending from the superior surface 942 to the inferior surface 944 of the spacer 912.

The first and second spacer portions 972, 974 may be joined together in any suitable manner. For example, the first and second spacer portions 972, 974 may be mated together by a splice joint, scarf joint, butt joint, or the like. The splice joint may include, for example, a half lap splice joint, a bevel lap splice joint, a tabled splice joint, or the like. In particular, the splice joint may include joining two pieces of material together by at least partially overlapping them (e.g., overlapping at least a portion of the first spacer portion 972 and at least a portion of the second spacer portion 974). In the embodiment shown in FIG. 11A, the joint portion between first and second spacer portions 972, 974 is at least partially a half lap splice joint such that the joint does not increase the height of the spacer 912. In a half lap splice joint, material is removed from each of the members so that the resulting joint is the thickness of the two members as combined. Although not shown, the splice joint between the first and second spacer portions 972, 974 may be beveled or scarfed, stepped, notched, keyed, nibbed, or the like. Any type of joint formed between the first and second spacer portions 972, 974 may be further secured with one or more pins 978 or the like.

The member 950 has an upper surface 962, a lower surface 964, a first lateral portion 966, a second lateral portion 968, and at least one hole 934 traversing the member 950 for receiving a fastener, such as a screw 930. The upper surface 962 and/or lower surface 964 may extend a distance beyond the superior surface 942, the inferior surface 944, or both surfaces 942, 944 of the spacer 912. In particular, a portion of member 950 may extend above or below the superior and inferior surfaces 942, 944 of the spacer 912. The projections of the upper and lower surfaces 962, 964 may each be in the form of an eyebrow 960. The eyebrow 960 may include a rounded portion, for example, with a smooth surface. The upper and lower surfaces 962, 964 may further include one or more torsional stabilizers 970 configured to prevent or minimize torsional motion of the implant 900 once implanted. The torsional stabilizers may be positioned, for example, substantially medially and laterally along the length of the member 950. The torsional stabilizers 970 may include a spiked or pointed projection or extension configured to engage adjacent vertebrae.

The member 950 is coupled to the spacer 912 such that the first end 972a of the first spacer portion 972 engages the first lateral portion 966 of the member 950 and the second end 974b of the second spacer portion 974 engages the second lateral portion 968 of the member 950. The spacer portions 972, 974 and the member 950 may also be joined together in any suitable manner. The member 950 may be configured to mirror the shape and design of the spacer 912. The spacer 912 may define at least one recess, projection, etc. sized and dimensioned to retain at least a portion of the member 950. Similar to the insert configurations discussed in this document, member 950 may rest against a portion of the spacer portions 972, 974 or a recess therein to form a joint, such as a lap joint, half lap joint, dovetail lap joint, beveled lap joint or scarf joint, stepped lap joint, tabled lap joint, or the like. In particular, at least a portion of the member 950 may at least partially overlap at least a portion of the spacer 912 or vice versa. In the embodiment shown in FIG. 11A, the joint portions between the member 950 and the spacer 912 are at least partially a half lap joint such that the joint does not increase the height of the spacer 912.

For example, the member 950 may include a first extension 967 extending from the first lateral portion 966 and a second extension (not visible) extending from the second lateral portion 968. The first extension 967 and second extension may extend posteriorly away from a front surface 965 of the member 950 and toward the distal end 946 of the spacer 912 when attached thereto. The first extension 967 may contact a first ledge 973 on the first spacer portion 972 to form a first half lap joint. Similarly, the second extension may contact a second ledge on the second spacer portion 974 to form a second half lap joint. The extensions 967 and ledges 973 may be configured to be complimentary and mate together, for example, with planar surfaces, curved surfaces, tapers, bevels, notches, or the like. Depending on the configuration of the joints, the joints may form a press-fit or friction-fit engagement to secure the member 950 to the spacer 912 or the joints may be further secured, for example, with adhesives, pins 978, or the like. For example, the first and second half lap joints may each be further secured with at least one pin 978.

When present, the pins 978 may traverse at least a portion of the spacer 912 and/or the member 950. For example, the extensions 967 may include one or more openings 980 extending therethrough sized and configured to receive a portion of pin 978 to secure the member 950 to the spacer 912. Similarly, the corresponding portion of the spacer 912 may include one or more openings 980 extending therethrough sized and configured to receive the remainder of pin 978 to secure the member 950 to the spacer 912. These openings 980 may or may not be threaded. The pins 978 may pass through holes 980, for example, in a substantially perpendicular manner relative to a horizontal plane to secure the joints between the member 950 and the spacer 912. For example, the pins 978 may be oriented substantially perpendicular relative to the superior and/or inferior surfaces 942, 944 of the spacer 912. The pins 978 may be in the form of dowels (as shown connecting the first spacer portion 972 to the second spacer portion 974) or may be at least partially threaded (as shown connecting the member 950 to the spacer 912). The pins 978 may be formed from a biocompatible material, such as titanium, or the pins 978 may be formed from tantalum, for example, to enable radiographic visualization.

The implant 900 may also include a locking mechanism 920 disposed on the member 950 for preventing back out of the screws 930. For example, a cam-style blocking mechanism may be used with screws 930 that capture the fixation device screws 930 once they are inserted fully through the member 950. As shown, the anti-back out mechanism 920 may include a single set screw 932 that retain the screws 930 with the implant 900, although any suitable anti-back out mechanism 920 may be selected by one of ordinary skill in the art.

FIGS. 12A-12E provide a twelfth embodiment of an implant 1000. In general, most of the structure of implant 1000 is similar or comparable to the structure of implant 1. In addition, this embodiment is substantially the same as the implant 900 discussed above, and the discussion for implant 900 applies equally here with the same reference numbers provided for unchanged elements. In this particular embodiment, the first and second spacer portions 1072, 1074 are connected together by a connector 1084 instead of being attached directly to one another. This allows the first and second spacer 1072, 1074 to be spaced apart with respect to one another. The connector 1084 may also be formed of a material different from the spacer portions 1072, 1074, for example, to allow for strength, support, radiographic visualization, or the like.

The first and second spacer portions 1072, 1074 may be secured together with one or more connectors 1084. The connector 1084 may be sized, shaped, and configured in any suitable manner to join the second end 1072b of the first spacer portion 1072 to the first end 1074a of the second spacer portion 1074. Any of the joints discussed in this document may be suitable to join the first and second spacer portions 1072, 1074 using connector 1084.

Figure 12A:
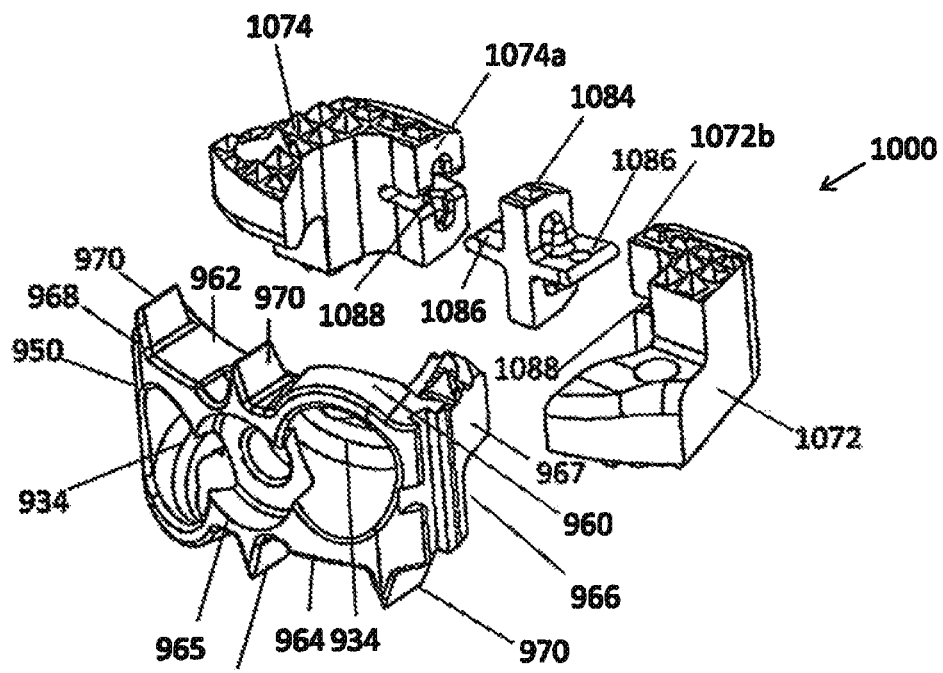
FIG. 12A shows an exploded view of a twelfth embodiment where the two-part spacer is joined by a connecting member.
Figure 12B:
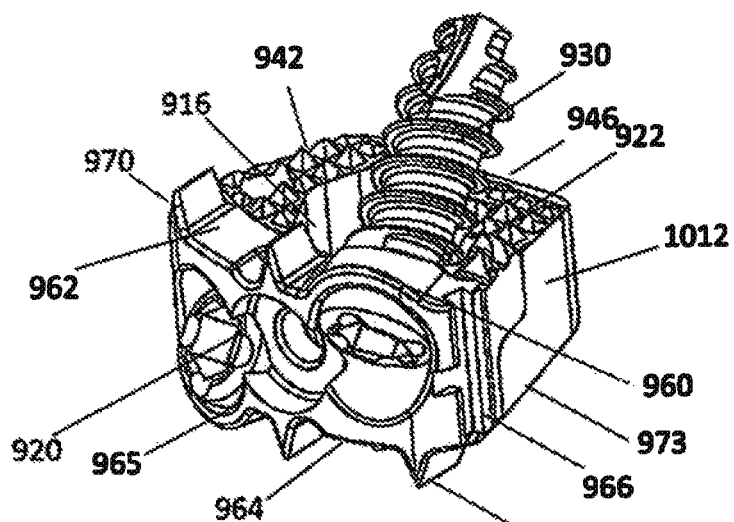
FIG. 12B shows a perspective view of the embodiment shown in FIG. 12A.
Figure 12C:
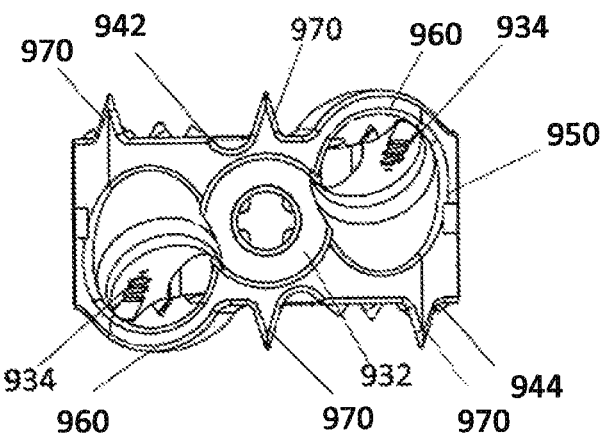
FIG. 12C is a front view of the embodiment shown in FIG. 12A.
Figure 12E:
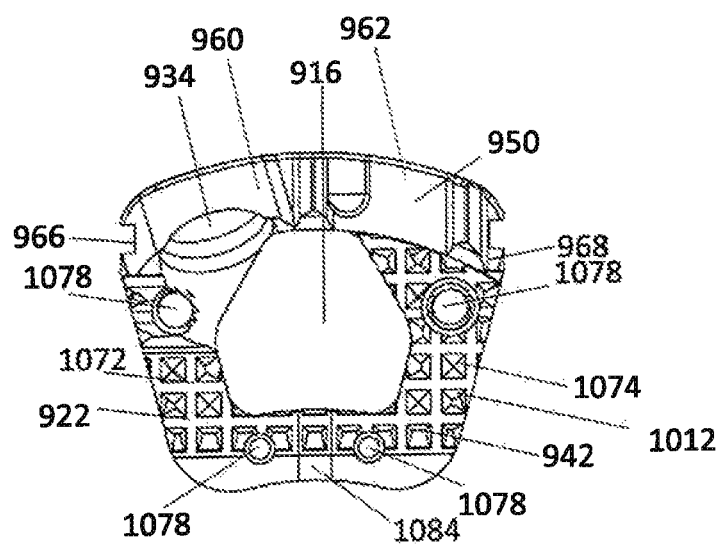
FIG. 12E is a top view of the embodiment shown in FIG. 12A.
Figure 12D:
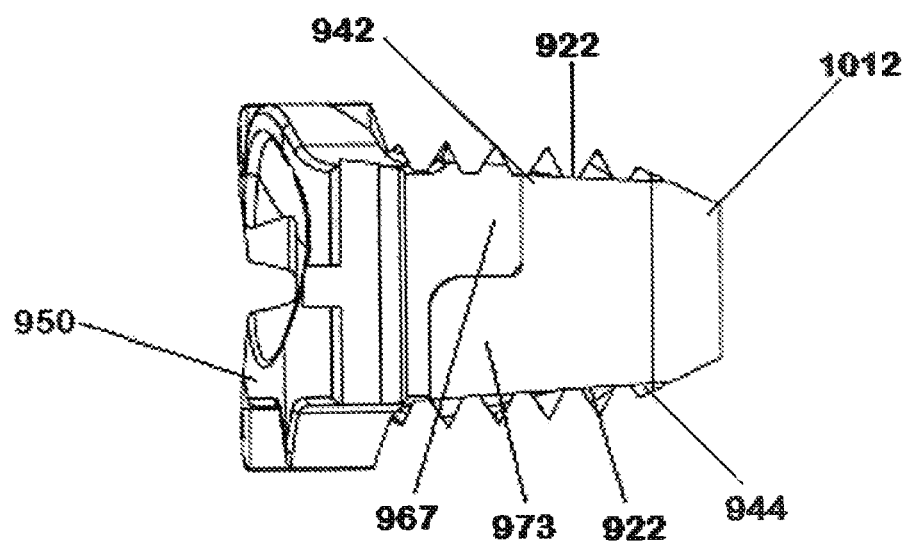
FIG. 12D is a lateral view of the embodiment shown in FIG. 12A.

In the embodiment depicted in FIG. 12A, the connector 1084 has a substantially t-shaped, plus-shaped, or cross-shaped configuration. For example, the connector 1084 may include at least first and second tenons 1086 sized and configured to be received within mortises 1088 in the spacer portions 1072, 1074. For example, a first tenon 1086 projecting laterally from the connector 1084 may be size and configured to be received within a first mortise 1088 in the second end 1072b of the first spacer portion 1072 and the second tenon 1086 projecting laterally in the other direction from the connector 1084 may be sized and configured to be received with the second mortise 1088 in the first end 1074a of the second spacer portion 1074.

The tenons 1086 may include additional superior and inferior projections, for example, which mate with a substantially t-shaped, plus-shaped, or cross-shaped mortise 1088. The mortise and tenon configuration may be of any suitable size, shape, and dimension to join the connector 1084 to the respective spacer portions 1072, 1074. As in the other embodiments, the joint may be further secured with one or more pins 1078. In particular, the pins 1078 may be positioned through each of the tenons 1086 to affix the connector 1084 to the respective spacer portions 1072, 1074. The pins 1078 may be positioned through openings 1080 in the tenons 1086 and corresponding openings 1080 in the spacer portions 1072, 1074.

According to a thirteenth embodiment shown in FIGS. 13A-13G, a single piece or unitary implant 1100 is provided with an anterior portion 1150 and a spacer portion 1112. Certain features of implant 1100 are similar or comparable to the structure of implant 1. In this embodiment, the inserts 50 have been replaced with an anterior portion 1150, and the spacer 1112 and the anterior portion 1150 form a one piece, standalone design.

The spacer 1112 has a superior surface 1142, an inferior surface 1144, a distal end 1146, a proximal end 1148, and first and second lateral sides 1136, 1138. The superior surface 1142 and the inferior surface 1144 each have a contact area 1122 configured to engage adjacent vertebrae. The contact areas 1122 may include one or more protrusions 1113 on the superior and inferior surfaces 1142, 1144 of each implant 1100 designed to grip the endplates of the adjacent vertebrae, resist migration, and aid in expulsion resistance. The plurality of protrusions 1113 may be pyramidal in shape and may form a series of ridges and grooves (as shown), but the protrusions 1113 can be configured to be any size or shape to enhance anchoring the spacer 1112 and the implant 1100 to each of the adjacent vertebrae.

The spacer 1112 defines an opening 1116 extending from the superior surface 1142 to the inferior surface 1144 of the spacer 1112 configured to receive bone graft materials. The spacer also defines openings 1117 extending through the lateral sides 1136, 1138 and into to the opening 1116. These lateral openings 1117 may be in fluid communication with the central opening 1116. These openings 1117 may be configured to allow for compression and expansion of the superior and inferior portions of the spacer 1112.

The distal end 1146 of the spacer 1112 may include a leading taper 1140 for ease of insertion into the disc space. The leading taper 1140 may be in the form of a chamfer or a bevel which enables self-distraction of the vertebral bodies during insertion of the implant 1100. The leading taper 1140 may be located along the insertion direction of the implant 100. For example, the leading taper 1140 may assist in an anterior approach to the disc space. The distal end 1146 may also include a groove or recess extending between the lateral sides 1136, 1138 to facilitate compression and expansion of the implant 1100.

The anterior portion 1150 has an upper surface 1162, a lower surface 1164, a first lateral portion 1166, a second lateral portion 1168, and at least one hole 1134 traversing the anterior portion 1150 for receiving a fastener, such as a screw 1130. At least a portion of the upper surface 1162 or the lower surface 1164 of the anterior portion 1150 extends beyond the superior surface 1142 or the inferior surface 1144 of the spacer 1112. The projections of upper surface 1162 and/or lower surface 1164 may be in the form of an eyebrow 1160. The eyebrow 1160 may include a rounded portion having a smooth surface. The upper surface 1162 and/or lower surface 1164 may further include one or more torsional stabilizers 1170 configured to prevent or minimize torsional motion of the implant 1100 once implanted. The torsional stabilizer 1170 may include a spiked or pointed projection or extension, for example, positioned medially and/or laterally on the anterior portion 1150.

Figure 13A:
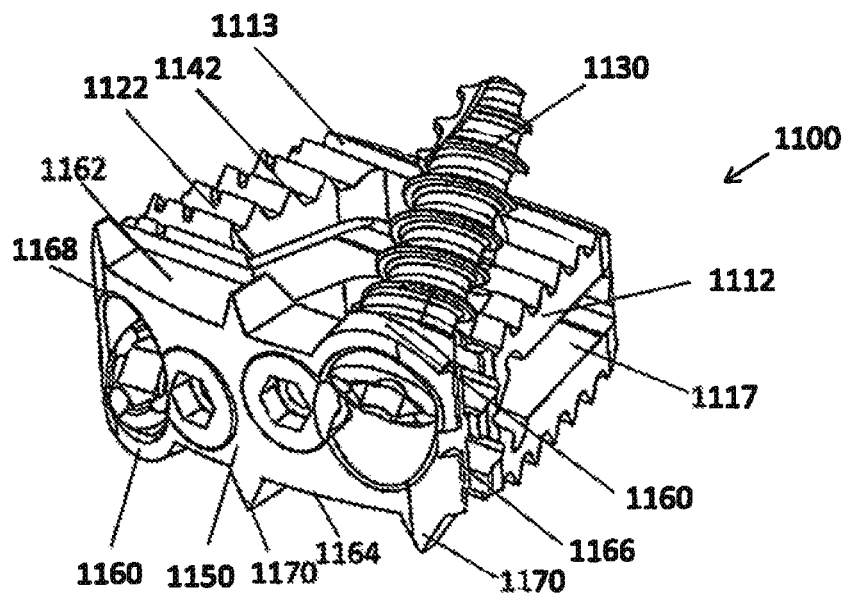
FIG. 13A is a perspective view from an anterior position of a thirteenth embodiment of a single piece implant having an anterior portion and a spacer portion.
Figure 13B:
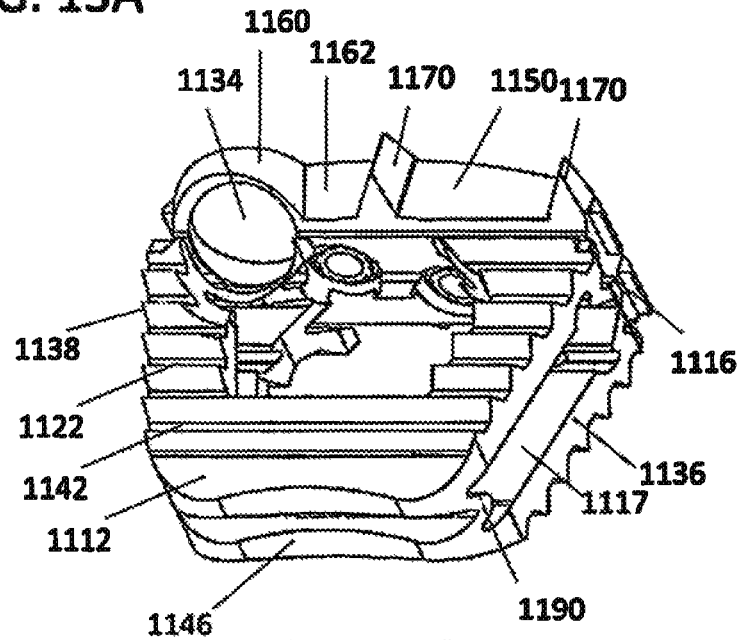
FIG. 13B is another perspective view from a posterior position of the embodiment shown in FIG. 13A.
Figure 13C:
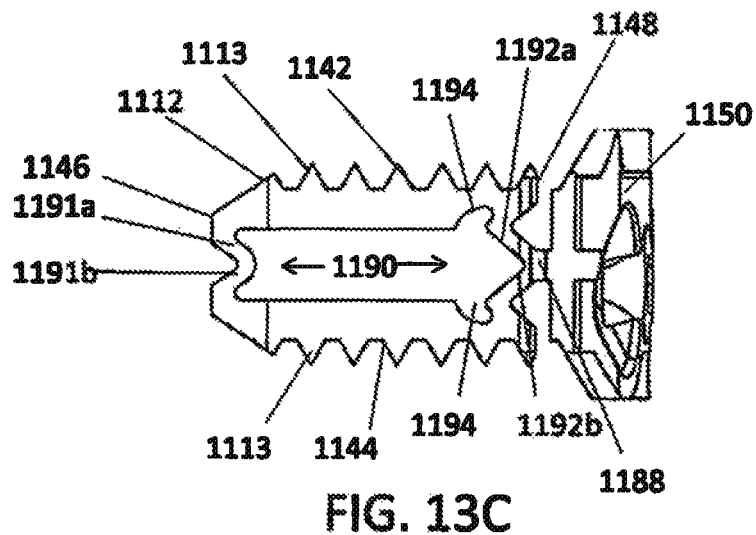
FIG. 13C is a lateral view of the embodiment shown in FIG. 13A.
Figure 13D:
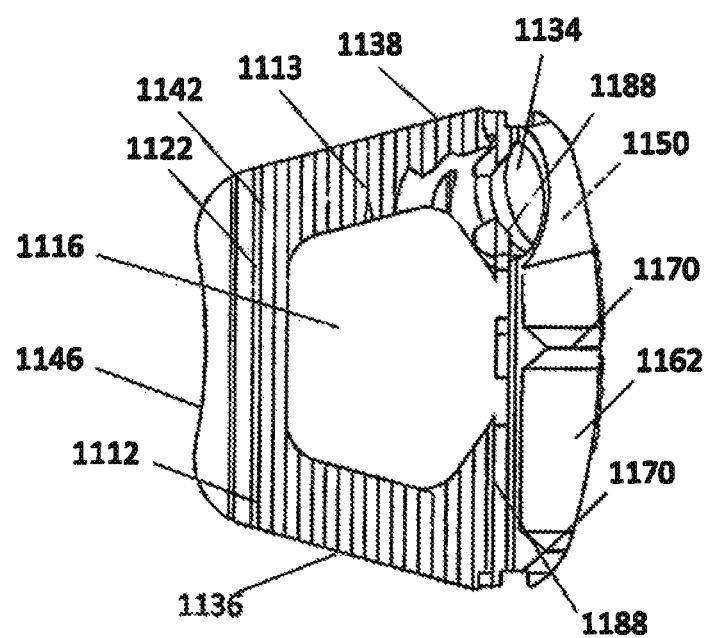
FIG. 13D is a top view of the embodiment shown in FIG. 13A.
Figure 13E:
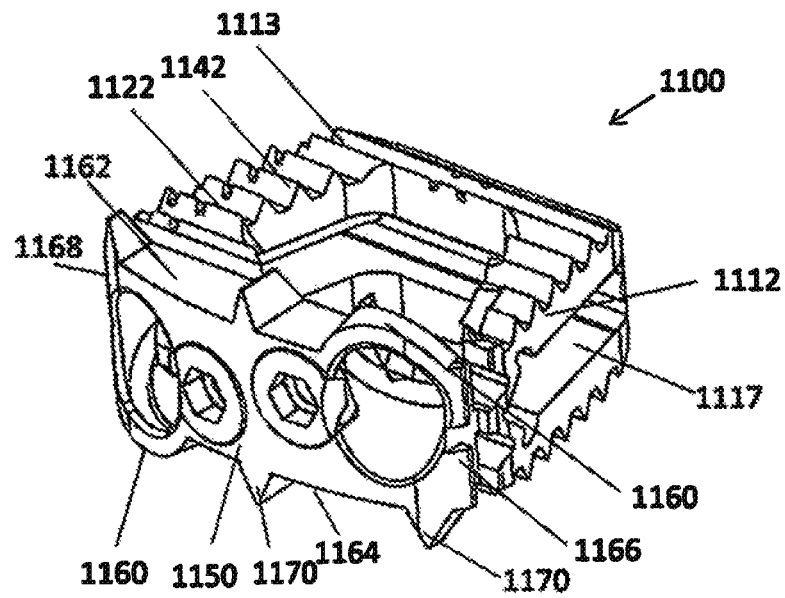
FIG. 13E is another perspective view of the embodiment shown in FIG. 13A.
Figure 13F:
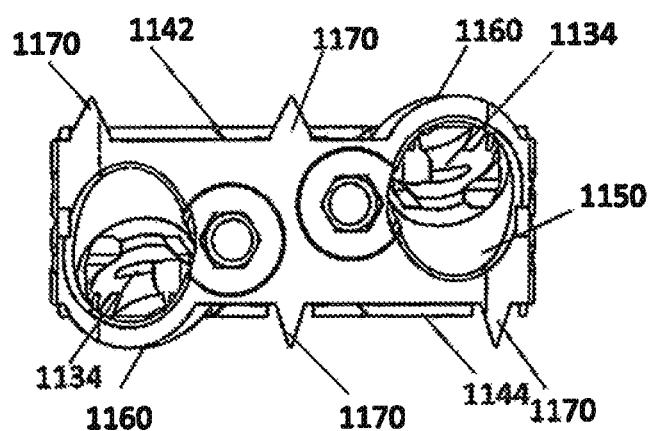
FIG. 13F is a front view of the embodiment shown in FIG. 13A.
Figure 13G:
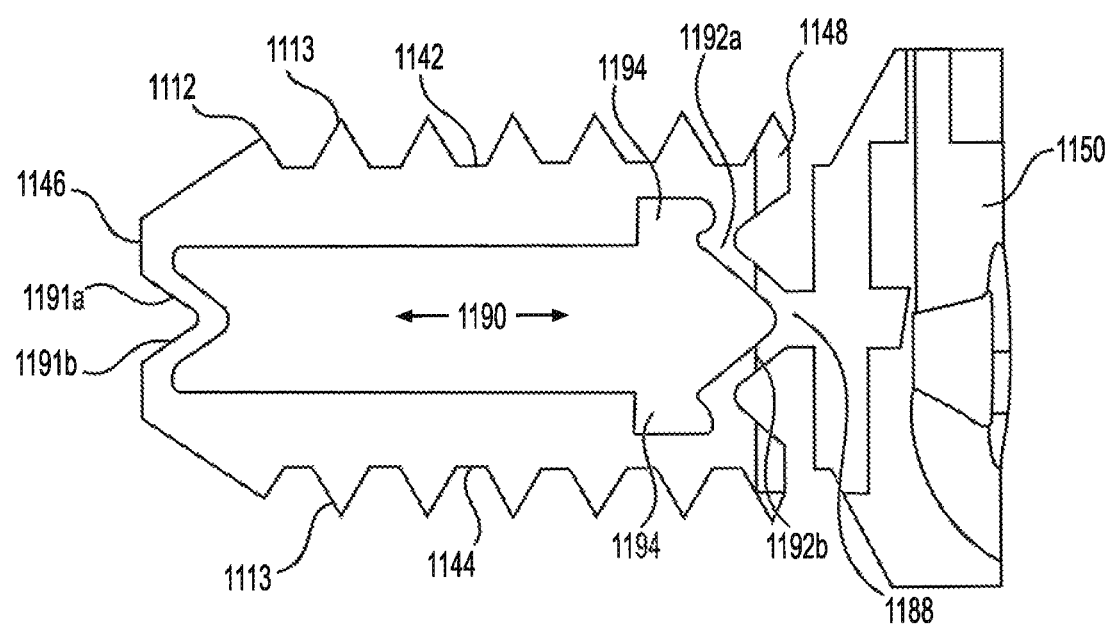
FIG. 13G is an alternative version of the embodiment shown in FIG. 13A.

The anterior portion 1150 extends from the proximal end 1148 of the spacer 1112 such that the anterior portion 1150 and the spacer 1112 are a single piece. As a single, unitary piece the anterior portion 1150 and the spacer 1112 may be formed from a single piece of material, such as titanium. By way of example as shown in FIGS. 13C and 13D, at least one beam 1188 may connect the anterior portion 1150 to the proximal end 1148 of the spacer 1112 to form a unitary piece. The beam 1118 may extend from a substantially medial position to a lateral position of the spacer 11112. The beam 1118 may extend across the entire width of the spacer 1112 or a portion thereof. The beam 1118 may be interrupted by a gap, for example, positioned substantially medially. No additional fixation devices or mechanisms are required to attach the anterior portion 1150 to the spacer portion 1112, but any suitable fixation systems may be selected by one of ordinary skill in the art.

The spacer 1112 includes one or more spring features 1190, for example, to allow for compression and/or expansion of the implant 1100. Thus, the spacer 1112 has a flexible nature with flexible sections or portions. In particular, the spring features 1190 are designed such that the spacer 1112 is able to mimic the properties of bone and/or PEEK especially when implanted between adjacent vertebrae. For example, the modulus of elasticity for bone, depending on the type, temperature, strain rate, and other factors, may range from about 0.5-25 GPa. In particular, cancellous bone has a modulus of elasticity of about 0.5-5 GPa. The Young's modulus of PEEK is about 3-4 GPa. Thus, PEEK is often used due to its bone-like modulus of elasticity. A solid block of titanium, on the other hand, has a much higher modulus of about 100-110 GPa. As a replacement to traditional PEEK implants, implant 1100 is provided with spring-like features 1190 such that the implant 1100, even when formed of titanium, can emulate the modulus of elasticity of cancellous bone. For example, the spacer 1112 may provide for a modulus of elasticity of about 0.5-5 GPa, about 1-5 GPa, about 2-5 GPa, or about 3-4 GPa for the implant 1100.

The spacer 1112 may provide for additional flexibility and an additional range of motion with respect to the two adjacent vertebrae. For example, the spacer 1112 may allow for at least two degrees of motion depending upon the direction and location of the applied force. In particular, the implant 1100 may allow for forward/anterior or aft/posterior bending and lateral bending to the left or right sides. This type of motion and flexibility may allow for more natural movement of the spinal column.

The spring features 1190 may be of any suitable design or configuration to provide compression and/or expansion of superior and inferior surfaces 1142, 1144 of the spacer 1112. For example, the spring feature 1190 may be in the form of a cantilevered v-spring having an elongated solid spring member with a cross-sectional configuration in the form of a V. As shown, the distal end 1146 of the spacer 1112 may have a first spring feature 1190. For example, the first spring feature 1190 may be in the form of a first v-spring. In addition, the proximal end 1148 of the spacer 1112 may include a second spring feature 1190. The second spring feature 1190 may also be in the form of a second v-spring. The first and second spring features 1190 may be the same or different. The first and second spring features 1190 may be configured such that the spacer 1112 simulates the modulus of elasticity of bone even when the spacer 1112 and the anterior portion 1150 are comprised of titanium or a titanium alloy.

As shown in FIG. 13C, the first spring feature 1190 on the distal end 1136 may include two longitudinal walls 1191a, 1191b provided with an angle therebetween. The angle between the two longitudinal walls 1191a, 1191b of the v-spring may range from about 45°-170°, about 60°-150°, about 80°-130°, or about 70°-100°, for example. The distal portions of the two longitudinal walls 1191a, 1191b may be anchored to the superior and inferior portions of the spacer 1112 by additional v-spring configurations. For example, the first longitudinal wall 1191a may interface with the superior portion of the spacer 1112 by a v-spring, which is inverted relative to the v-spring provided between the first and second longitudinal walls 1191a, 1191b. Similarly, the second longitudinal wall 1191b may interface with the inferior portion of the spacer 1112 by another v-spring, which is inverted relative to the v-spring provided between the first and second longitudinal walls 1191a, 1191b. Thus, the first spring feature 1190 provided on the distal end 1136 may include a zig-zag of three v-springs oriented in opposite directions. The angle of the v-spring between the first and second longitudinal walls 1191a, 1191b may be greater than the angles connecting the respectively longitudinal walls 1191a, 1191b to the superior and inferior portions of the spacer 1112.

The implant 1100 may include a second spring feature 1190 on the proximal end 1148 of the spacer 1112. The second spring feature 1190 may also include two longitudinal walls 1192a, 1192b provided with an angle therebetween. The angle between the two longitudinal walls 1192a, 1192b of the v-spring may again range from about 45°-170°, about 60°-150°, about 80°-130°, or about 70°-100°, for example. This angle may be the same, larger, or smaller than the angle between the first and second longitudinal walls 1191a, 1191b at the distal end 1136. The apex of the angle may form a junction to connect with the beam 1188, which connects the spacer portion 1112 to the anterior portion 1150.

The distal portions of the two longitudinal walls 1192a, 1192b may be anchored to the superior and inferior portions of the spacer 1112, respectively by additional v-spring configurations. For example, the first longitudinal wall 1192a may interface with the superior portion of the spacer 1112 by a v-spring, which is inverted relative to the v-spring provided between the first and second longitudinal walls 1192a, 1192b. Similarly, the second longitudinal wall 1192b may interface with the inferior portion of the spacer 1112 by another v-spring, which is inverted relative to the v-spring provided between the first and second longitudinal walls 1192a, 1192b. Thus, the second spring feature 1190 provided on the proximal end 1148 may include a zig-zag of three v-springs oriented in opposite directions. The angle of the v-spring between the first and second longitudinal walls 1192a, 1192b may be the same or greater than the angles connecting the respectively longitudinal walls 1192a, 1192b to the superior and inferior portions of the spacer 1112. Additional recesses 1194 may be provided on the superior and inferior portions of the spacer 1112 to allow for proper movement of the v-springs. In particular, the recesses 1194 may be formed such that the apexes of the upper and lower v-portions are revealed. As shown in FIG. 13C, the recesses 1194 may be rounded or curved. In an alternative embodiment shown in FIG. 13G, the recesses 1194 may be angled or pointed.

Although a v-shaped spring is exemplified in this embodiment, the spring portions 1190 may be formed in any suitable shape or configuration not limited to the v-shape, and may include, for example, U-shape, S-shape, coiled, square, rectangular, sinusoidal, corrugated and accordion pleated. In addition, the shape of the spring features 1190 may be symmetrical or non-symmetrical. For example, the longitudinal walls 1191a, 1191b, 1192a, 1192b may be symmetrical or non-symmetrical with respect to one another.

Figure 14:
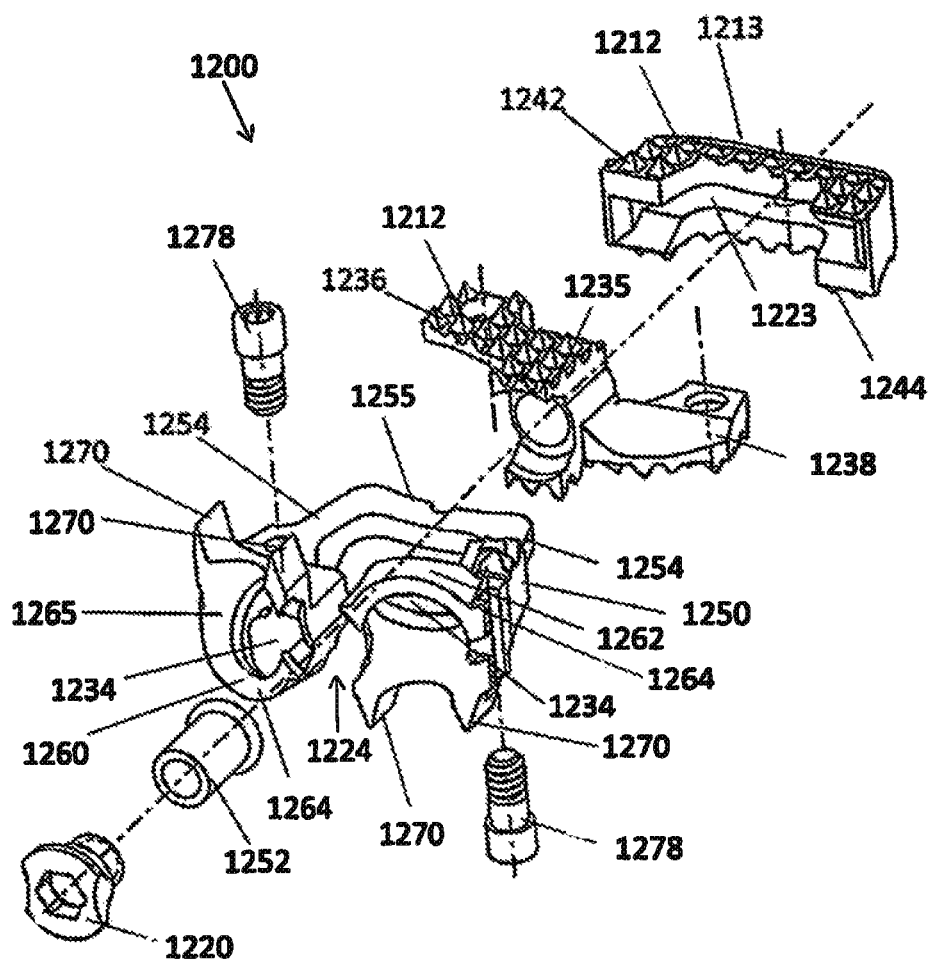
FIG. 14 is an exploded view of a fourteenth embodiment of an implant having a frame with endplates configured to be affixed thereto.

According to a fourteenth embodiment shown in FIG. 14, which may be particularly suitable for an anterior cervical procedure, an implant 1200 including a frame 1250 with one or more endplates 1212 is provided. FIG. 14 depicts an exploded view of the implant 1200. The frame 1250 may be substantially in the form of a split-ring or partial loop of material with a central opening. When combined with the endplates 1212, which may be shaped and configured to match the central opening in the frame 1250, the opening may provide for a graft opening area configured to provide the maximum amount of volume for bone graft packing. The graft area may be configured for receiving bone graft material, for example, to promote fusion of the adjacent vertebral bodies.

The frame 1250 may include a front portion 1265. The front portion 1265 may define one or more fastener apertures 1234 configured to secure fasteners, such as bone screws (not shown), in both the superior and inferior vertebrae. The front portion 1265 may be a unitary piece or may be divided into two separate portions with a passage or gap 1224 positioned therebetween. The front portion 1265 may include an upper surface 1262 and a lower surface 1264. A first arm 1254 may extend from a first end of the front portion 1265 and a second arm 1254 may extend from a second end of the front portion 1265 of the frame 1250. The arms 1254 may join together to form the full or partial ring-like structure. The frame 1250 may also include a rear portion 1255. The arms 1254 may meet at the rear portion 1255 of the frame 1250, for example. The front portion 1265 may have a height greater than the height of the arms 1250 and the rear portion 1255.

One or more endplates 1212 are positioned on and affixed to the frame 1250 such that at least a portion of the ring portion of the frame 1250 is covered or housed within the endplates 1212. Preferably, the front portion 1265 of the frame 1250 is not covered by the endplates 1212. The endplates 1212 may form a superior surface 1242 and an inferior surface 1244 configured to contact and engage adjacent vertebrae (not shown). The superior and inferior surfaces 1242, 1244 may be parallel, curved, or angled to help restore or recreate a lordosis angle (or other angle) of the human spine. In addition, the superior and/or inferior surfaces 1242, 1244 may be contoured to conform more closely to the concave endplates of the adjacent vertebra.

In order to engage the adjacent vertebrae, the endplates 1212 may include a plurality of protrusions 1213 or teeth on the contact areas of the superior and/or inferior surfaces 1242, 1244. The protrusions 1213 may help to grip the endplates of the adjacent vertebrae, resist migration, and aid in expulsion resistance. The plurality of protrusions 1213 may be pyramidal in shape, but the protrusions 1213 can be configured to be any size or shape to enhance anchoring of the implant 1200 to each of the adjacent vertebrae.

As shown in FIG. 14, two endplates 1212 may be provided. A first endplate 1212 may have a substantially c-shaped configuration designed to follow the shape of the rear portion 1255 of the frame 1350. The endplate 1212 may include a recess or channel 1223 designed and configured to retain at least a portion of the ring and, in particular, at least the rear portion 1255 and a portion of the arms 1254 of the frame 1250. This endplate 1212 may also include a leading taper configured to ease insertion of the implant 1200 into the disc space.

A second endplate 1212 may be provided to at least partially reside within the passage or gap 1224 in the front portion 1265 of the frame 1250. In particular, this endplate 1212 may include a central portion 1235 sized and configured to fit within the gap 1224. The central portion 1235 may form a portion of the superior surface 1242 (e.g., having protrusions 1213 extending superiorly) and a portion of the inferior surface 1244 (e.g., having protrusions 1213 extending inferiorly). In addition, the central portion 1235 may include an opening sized and configured to receive an insert 1252 which accepts an anti-backout locking mechanism 1220. The locking mechanism 1220 may be provided to block or unblock the heads of the fasteners or screws when positioned within the respective fastener apertures 1234. The anti-back out mechanism 1220 may include, for example, a set screw configured to block a portion of the fasteners positioned through the frame 1250.

In addition to the central portion 1235, the endplate 1212 may also include a first lateral wing 1236 and a second lateral wing 1238. The first lateral wing 1236 may be configured to contact a first side of one of the arms 1254 and the second lateral wing 1238 may be configured to contact a second side of the other arm 1254. In this manner, the endplate 1212 may be positioned such that the first lateral wing 1236 forms a portion of the superior surface 1242 (e.g., having protrusions 1213 extending superiorly) and the second lateral wing 1238 forms a portion of the inferior surface 1244 (e.g., having protrusions 1213 extending inferiorly). It is envisioned that the positions of the wings 1236, 1238 may be changed or reversed as one of ordinary skill in the art may recognize.

One or more of the endplates 1212 may be secured to the frame 1250 using any of the mechanisms or techniques described herein. In particular, one or more of the endplates 1212 may be secured with one or more pins 1278. Any suitable number, type, and location for the pins 1278 may be selected. For example, two pins 1278 may be positioned within openings located adjacent to and on opposite sides of the front portion 1265 of the frame 1250.

In this embodiment, the frame 1250 provides two fastener apertures 1234 to secure fasteners, such as bone screws, in both the superior and inferior vertebrae. For example, the fastener apertures 1234 may extend through the front portion 1265 of the frame 1250 at an angle. A portion of the upper and/or lower surfaces 1262, 1264 of the frame 1250 may extend a distance beyond the superior surface 1242, the inferior surface 1244, or both surfaces 1242, 1244 of the endplates 1212. The projections of the upper and lower surfaces 1262, 1264 of the frame 1250 may be in the form of eyebrows 1260. In this embodiment, the eyebrows 1260 include a substantially smooth and curved surface. One or more torsional stabilizers 1270 may also be provided and configured to prevent or minimize torsional motion of the implant 1200 once implanted. The torsional stabilizers 1270 may include a spiked or pointed projection or extension configured to engage adjacent vertebrae.

Figure 15A:
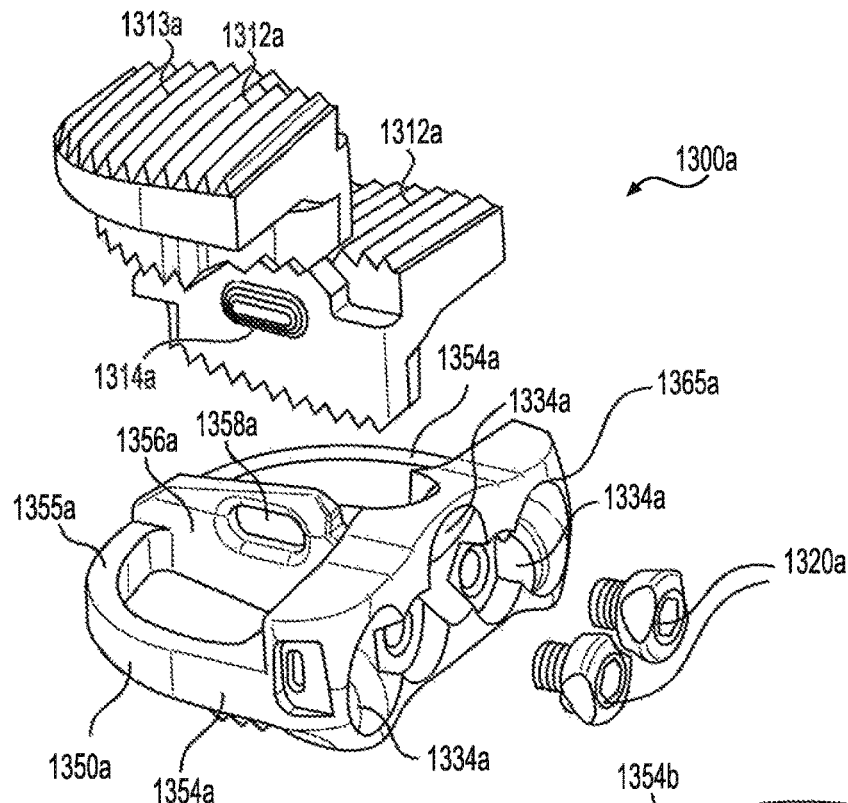
FIGS. 15A and 15B are exploded views of a fifteenth embodiment showing implants having a frame defining a ring-like shape where the endplates are secured with an interference fit.
Figure 15B:
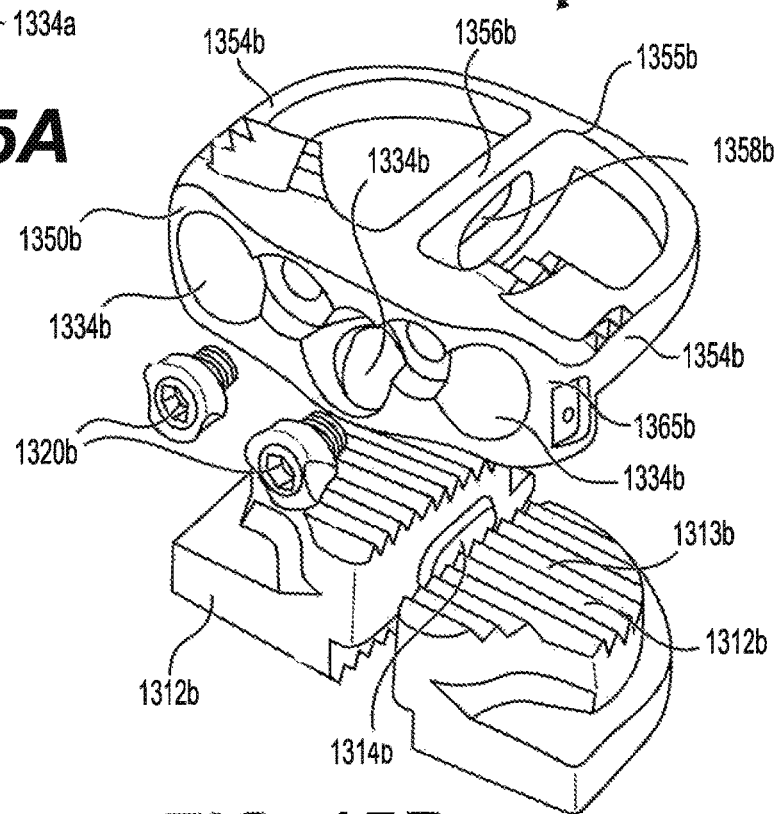

According to a fifteenth embodiment shown in FIGS. 15A and 15B, which may be particularly suitable for an anterior lumbar procedure, implants 1300*a*, 1300*b* include a frame 1350*a*, 1350*b* with one or more endplates 1312*a*, 1312*b*. FIGS. 15A and 15B depict exploded views of the implants 1300*a*, 1300*b*. The frames 1350*a*, 1350*b* may be substantially in the form of a ring or loop of material with a central opening divided into two equal halves. The endplates 1312*a*, 1312*b*, for example, in the form of PEEK or allograft spacers, may be sized and configured to fit within the openings.

The frames 1350*a*, 1350*b* may each include a front portion 1365*a*, 1365*b*, which defines one or more fastener apertures 1334*a*, 1334*b* configured to secure fasteners, such as bone screws (not shown), in both the superior and inferior vertebrae. The front portion 1365*a*, 1365*b* may extend from a first lateral end to a second lateral end of the frame 1350*a*, 1350*b*. A first arm 1354*a*, 1354*b* may extend from a first end of the front portion 1365*a*, 1365*b* and a second arm 1354*a*, 1354*b* may extend from a second end of the front portion 1365*a*, 1365*b* of the frame 1350*a*, 1350*b*. The arms 1354*a*, 1354*b* may join together to form the ring-like structure of the frame 1350*a*, 1350*b*. The frame 1350*a*, 1350*b* may include a rear portion 1355*a*, 1355*b* where the arms 1354*a*, 1354*b* connect together.

In this embodiment, the frame 1350a, 1350b provides three fastener apertures 1334a, 1334b to secure fasteners, such as bone screws, in both the superior and inferior vertebrae. For example, the fastener apertures 1334a, 1334b may extend through the front portion 1365a, 1365b of the frame 1350a, 1350b at an angle. As described herein, once inserted through the fastener apertures 1334a, 1334b, the fasteners may be secured with an anti-back out prevention or locking mechanism 1320a, 1320b, such as by using one or more blocking screw to capture a portion of the fasteners to prevent back out.

The frame 1350a, 1350b may also include a support member 1356a, 1356b. The support member 1356a, 1356b may divide or segment the central opening and provide stability to the frame 1350a, 1350b. As shown, the support member 1356a, 1356b may be a medial portion of the implant 1300a, 1300b, which is positioned centrally to divide the central opening into two equal halves. It is envisioned, however, that the support member 1356a, 1356b may be absent creating a single large opening, the support member 1356a, 1356b may be offset such that the two openings are not equal in size, or more than one support member 1356a, 1356b may be provided to create multiple openings for the endplates 1312a, 1312b to reside. The support member 1356a, 1356b may also have at least one opening 1358a, 1358b extending therethrough to retain a corresponding protrusion 1314a, 1314b on the endplates 1312a, 1312b. The opening 1358a, 1358b in the support member 1356a, 1356b may be elongated with a curved or beveled perimeter designed to provide an interference fit when the endplate 1312a, 1312b is snapped into the openings of the frame 1350a, 1350b. Although a single opening 1358a, 1358b in the support member 1356a, 1356b is shown, additional openings may also be provided to secure the endplates 1312a, 1312b. In addition or alternatively, similar openings may be provided in the arms 1354a, 1354b of the frame 1350a, 1350b to secure the endplates 1312a, 1312b. The front portion 1365a, 1365b may have a height greater than the height of the arms 1354a, 1354b and/or the rear portion 1355a, 1355b. In addition, the support member 1356a, 1356b may have a height greater than the height of the arms 1354a, 1354b.

One or more endplates 1312a, 1312b are positioned on and affixed to the frame 1350a, 1350b such that at least a portion of the endplates 1312a, 1312b is received within the openings in the frame 1350a, 1350b. The endplates 1312a, 1312b may be inserted from the top or the bottom of the implant 1300a, 1330b. The endplates 1312a, 1312b may include upper and lower surfaces configured to contact and engage adjacent vertebrae (not shown). The upper and lower surfaces may be parallel, curved, or angled to help restore or recreate a lordosis angle (or other angle) of the human spine. In addition, the upper and/or lower surfaces may be contoured to conform more closely to the concave endplates of the adjacent vertebra.

The endplates 1312a, 1312b may be L-shaped with a stepped configuration, for example, or may include a raised portion sized and configured to fit within the central opening of the frame 1350a, 1350b. For example, the raised portion may form a portion of the upper and/or lower surfaces. This configuration may allow for the endplates 1312a, 1312b to bottom out on the frame 1350a, 1350b preventing excessive force from pushing the endplates 1312a, 1312b out the other end of the implant 1300a, 1300b upon insertion. The endplates 1312a, 1312b may include a plurality of protrusions 1313a, 1313b or teeth on the contact areas of the upper and/or lower surfaces to engage the adjacent vertebrae. The protrusions 1313a, 1313b may help to grip the endplates of the adjacent vertebrae, resist migration, and aid in expulsion resistance. The plurality of protrusions 1313a, 1313b may be pyramidal in shape and may form a series of ridges and grooves (as shown), but the protrusions 1313a, 1313b can be configured to be any size or shape to enhance anchoring the implant 1300a, 1300b to each of the adjacent vertebrae.

As shown in FIGS. 15A and 15B, two endplates 1312a, 1312b may be provided for each implant 1300a, 1300b. The endplates 1312a, 1312b for each respective implant 1300a, 1300b may be mirror images of one another. The endplates 1312a, 1312b may include a lateral surface having at least one protrusion 1314a, 1314b extending outwardly therefrom. The edges of the protrusion 1314a, 1314b may be chamfered or beveled such that the protrusion 1314a, 1314b provides an interference fit with the opening 1358a, 1358b in the support member 1356a, 1356b. Although depicted with the protrusions 1314a, 1314b, the endplates 1312a, 1312b may be secured to the frame 1350a, 1350b using any of the mechanisms or techniques described herein.

Figure 16A:
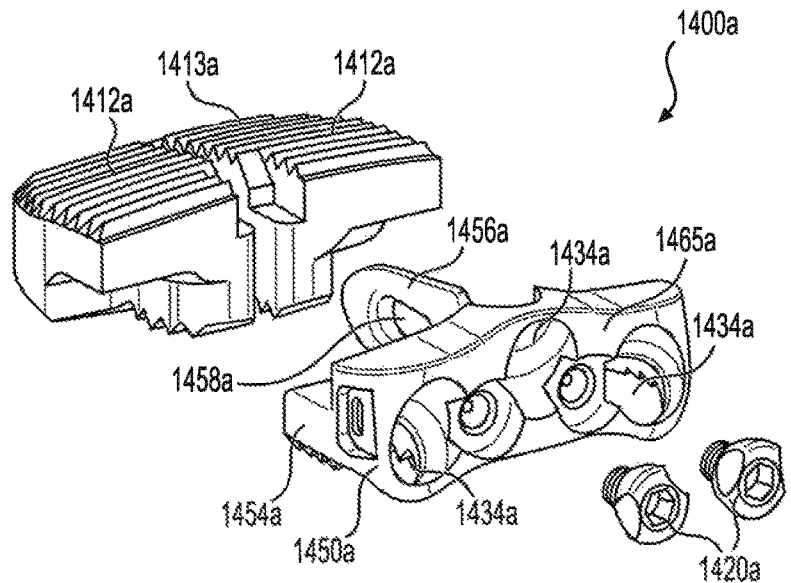
FIGS. 16A and 16B show exploded views of a sixteenth embodiment including implants having a frame including arms and a support member where the endplates are secured with an interference fit.
Figure 16B:
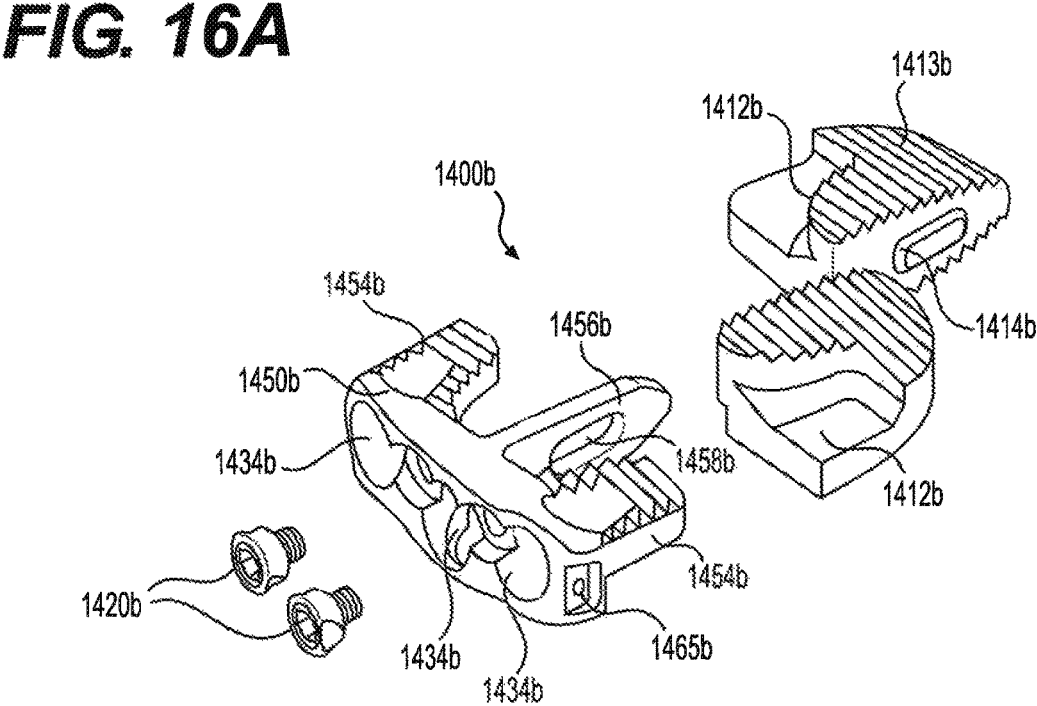

A sixteenth embodiment is shown in FIGS. 16A and 16B, which depict exploded views of implants 1400a, 1400b. This embodiment is substantially the same as the implants 1300a, 1300b discussed above, and the discussion for implants 1300a, 1300b applies equally here. In this particular embodiment, implants 1400a, 1400b include a frame 1450a, 1450b with one or more endplates 1412a, 1412b. Instead of forming a ring or loop, the frame 1450a, 1450b includes extensions or arms 1454a, 1454b and support member 1456a, 1456b to secure the endplates 1412a, 1412b. The endplates 1412a, 1412b may be in the form of PEEK or allograft spacers, for example, sized and configured to fit within the openings or channels defined between the arms 1454a, 1454b and support member 1456a, 1456b.

The front portion 1465a, 1465b of the frame 1450a, 1450b defines one or more fastener apertures 1434a, 1434b configured to secure fasteners, such as bone screws (not shown), in both the superior and inferior vertebrae. In this embodiment, the frame 1450a, 1450b provides three fastener apertures 1434a, 1434b extending through the front portion 1465a, 1465b of the frame 1450a, 1450b at an angle to secure fasteners, such as bone screws, in both the superior and inferior vertebrae. As described herein, once inserted through the fastener apertures 1434a, 1434b, the fasteners may be secured with an anti-back out prevention or locking mechanism 1420a, 1420b, such as by using one or more blocking screw to capture a portion of the fasteners to prevent back out.

The frame 1450a, 1450b may include a first arm 1454a, 1454b extending from a first end of the front portion 1465a, 1465b and a second arm 1454a, 1454b extending from a second end of the front portion 1465a, 1465b. A support member 1456a, 1456b may be positioned between the arms 1454a, 1454b. As shown, the support member 1456a, 1456b may be positioned at a medial portion of the implant 1400a, 1400b, and may be positioned centrally between the arms 1454a, 1454b. It is envisioned, however, that the support member 1456a, 1456b may be absent creating a single large opening, the support member 1456a, 1456b may be offset creating unequally sized openings, or more than one support member 1456a, 1456b may be provided to create multiple locations for the endplates 1412a, 1412b to reside.

The support member 1456a, 1456b may also have at least one opening 1458a, 1458b extending therethrough to retain a corresponding protrusion 1414b (protrusion not visible in FIG. 16A) on the endplates 1412a, 1412b. The opening 1458a, 1458b in the support member 1456a, 1456b may be elongated with a curved or beveled perimeter designed to provide an interference fit when the endplate 1412a, 1412b is snapped into openings or channels between the arms 1454a, 1454b and support member 1456a, 1456b. Although a single opening 1458a, 1458b in the support member 1456a, 1456b is shown, additional openings may also be provided to secure the endplates 1412a, 1412b. In addition or alternatively, similar openings may be provided in the arms 1454a, 1454b of the frame 1450a, 1450b to secure the endplates 1412a, 1412b.

One or more endplates 1412a, 1412b are configured to be positioned on and/or affixed within openings or channels between the arms 1454a, 1454b and support member 1456a, 1456b. The endplates 1412a, 1412b may be inserted from the top, bottom, or back of the implant 1400a, 1400b. The endplates 1412a, 1412b may include upper and lower surfaces configured to contact and engage adjacent vertebrae (not shown). The upper and lower surfaces may be parallel, curved, or angled to help restore or recreate a lordosis angle (or other angle) of the human spine. In addition, the upper and/or lower surfaces may be contoured to conform more closely to the concave endplates of the adjacent vertebra.

The endplates 1412a, 1412b may be notched or provided with a stepped configuration or may include a raised portion sized and configured to fit between the arms 1454a, 1454b and support member 1456a, 1456b. This configuration may allow for the endplates 1412a, 1412b to bottom out on the frame 1450a, 1450b preventing excessive force from pushing the endplates 1412a, 1412b out the other end upon insertion. The endplates 1412a, 1412b may include protrusions 1413a, 1413b or teeth on the contact areas of the implant 1400a, 1400b as discussed herein.

As shown in FIGS. 16A and 16B, two endplates 1412a, 1412b may be provided for each implant 1400a, 1400b. The endplates 1412a, 1412b for each respective implant 1400a, 1400b may be mirror images of one another. The endplates 1412b may include a lateral surface having at least one protrusion 1414b extending outwardly therefrom. Similar protrusions are provided on endplates 1412a in FIG. 16A, which are not visible in the view provided. The edges of the protrusion 1414b may be chamfered or beveled to provide an interference fit with the opening 1458b in the support member 1456b. Although shown to be secured with the protrusions 1414b, the endplates 1412a, 1412b may be additionally or alternatively secured to the frame 1450a, 1450b using any of the mechanisms or techniques described herein.

Figure 17A:
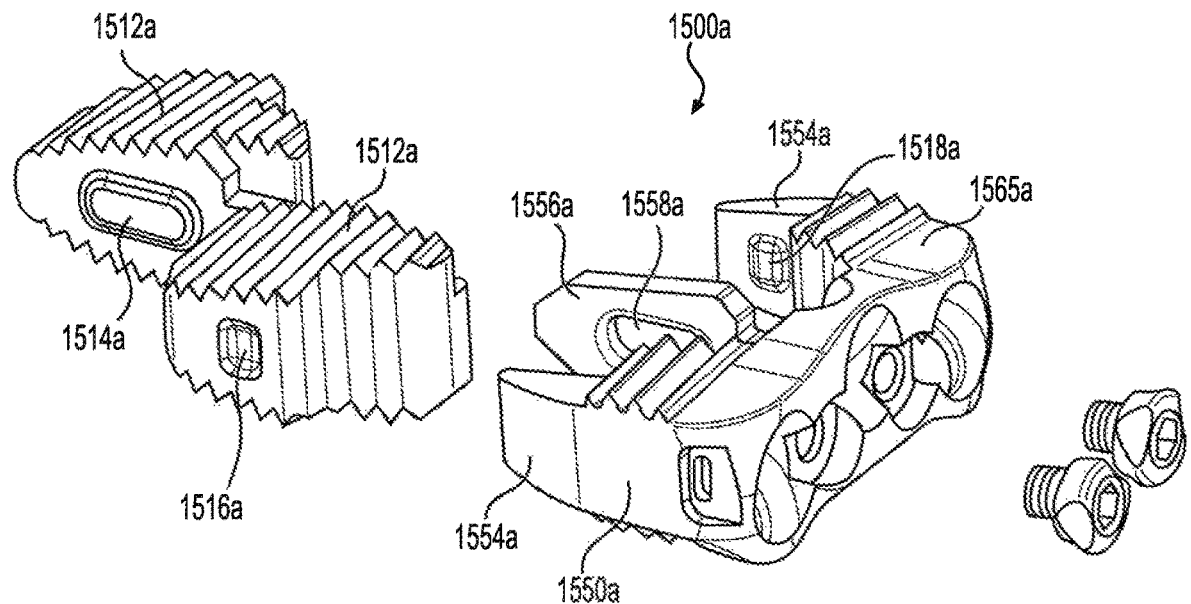
FIGS. 17A and 17B show exploded views of a seventeenth embodiment including implants having a frame including arms and a centrally located support member and two endplates securable with interference features on the support member and the arms.
Figure 17B:
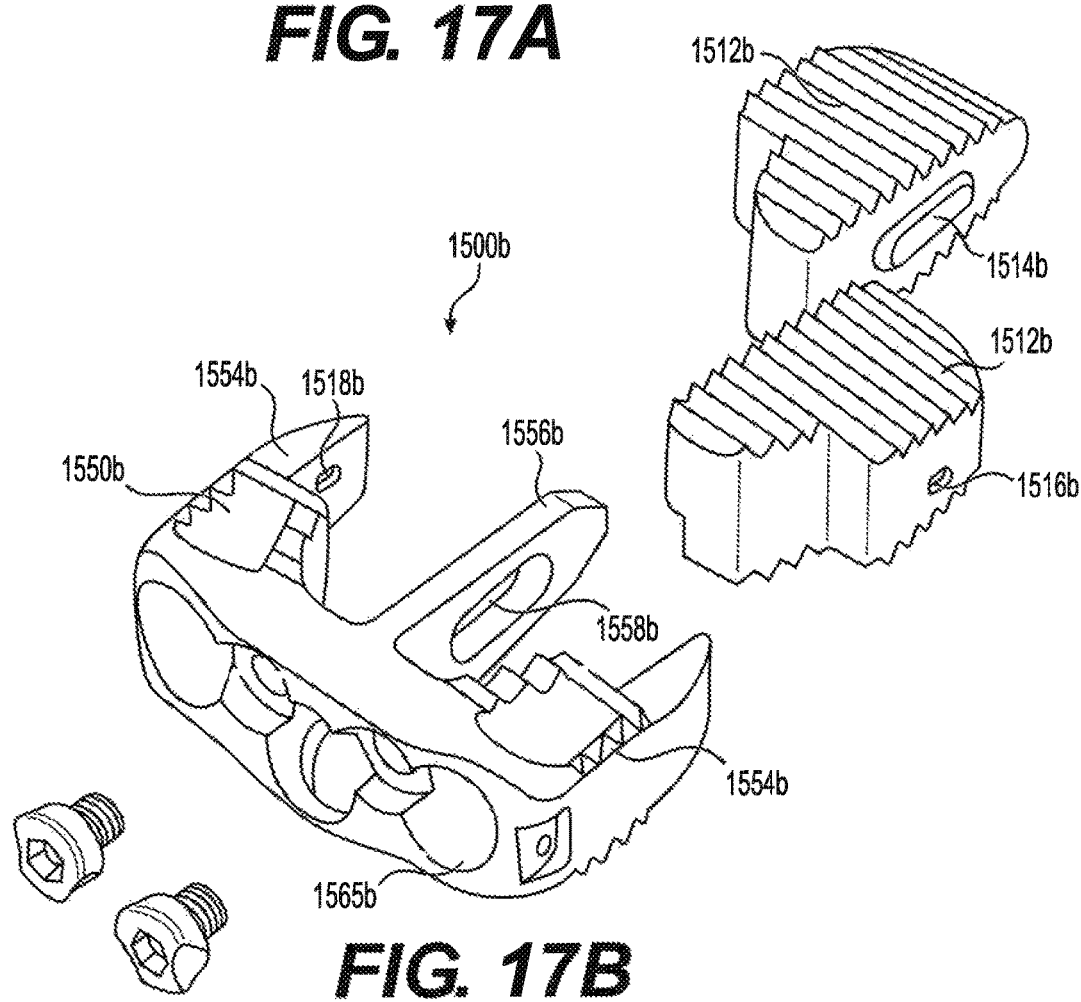

As shown in FIGS. 17A and 17B, a seventeenth embodiment includes exploded views of implants 1500a, 1500b. This embodiment is substantially the same as the implants 1400a, 1400b discussed above, and the discussion for implants 1400a, 1400b applies equally here. Implants 1500a, 1500b include a frame 1550a, 1550b with one or more endplates 1512a, 1512b configured to be positioned between the extensions or arms 1554a, 1554b and support member 1556a, 1556b to secure the endplates 1512a, 1512b. This embodiment includes protrusions 1514a, 1514b on the medial portion of the endplate 1512a, 1512b as well as indentations 1516a, 1516b on the lateral portion of the endplate 1512, 1512b to provide an interference fit with the frame 1550a, 1550b. The endplates 1512a, 1512b may be in the form of PEEK or allograft spacers, for example, sized and configured to fit within the openings or channels between the arms 1554a, 1554b and support member 1556a, 1556b.

The frame 1550a, 1550b may include a first arm 1554a, 1554b extending from a first end of the front portion 1565a, 1565b and a second arm 1554a, 1554b extending from a second end of the front portion 1565a, 1565b. The support member 1556a, 1556b may be positioned between the arms 1554a, 1554b, for example, at a central location between the arms 1554a, 1554b. The support member 1556a, 1556b may have at least one opening 1558a, 1558b extending therethrough to retain a corresponding protrusion 1514a, 1514b on the medial portion of the endplates 1512a, 1512b. The opening 1558a, 1558b in the support member 1556a, 1556b may be elongated with a curved or beveled perimeter designed to provide an interference fit when the endplate 1512a, 1512b is snapped into openings or channels between the arms 1554a, 1554b and support member 1556a, 1556b. The lateral portion of the endplates 1512a, 1512b may include at least one indentation 1516a, 1516b therein to retain a corresponding protrusion 1518a, 1518b on an interior surface of the arms 1554a, 1554b. The indentation 1516a, 1516b in the endplates 1512a, 1512b may be substantially square with a curved or beveled perimeter designed to provide an interference fit when the endplate 1512a, 1512b is snapped into openings or channels between the arms 1554a, 1554b and support member 1556a, 1556b. The protrusions 1514a, 1514b on the endplates 1512a, 1512b may be larger in size and shape than the protrusions 1518a 1518b on the arms 1554a, 1554b, for example. Although it is envisioned that any size, shape, dimension, and position for the protrusions 1514a, 1514b, 1518a, 1518b may be selected by one of ordinary skill in the art.

The endplates 1512a, 1512b may be notched and contoured to fit between the arms 1554a, 1554b and support member 1556a, 1556b. As shown in FIGS. 17A and 17B, two endplates 1512a, 1512b may be provided for each implant 1500a, 1500b. The endplates 1512a, 1512b for each respective implant 1500a, 1500b may be mirror images of one another. The endplates 1512a, 1512b may be inserted from the top, bottom, or back of the implant 1500a, 1500b. The endplates 1512a, 1512b may include upper and lower surfaces configured to contact and engage adjacent vertebrae (not shown). The upper and lower surfaces may be parallel, curved, angled, contoured, or the like to conform more closely with the endplates of the adjacent vertebra.

Figure 18A:
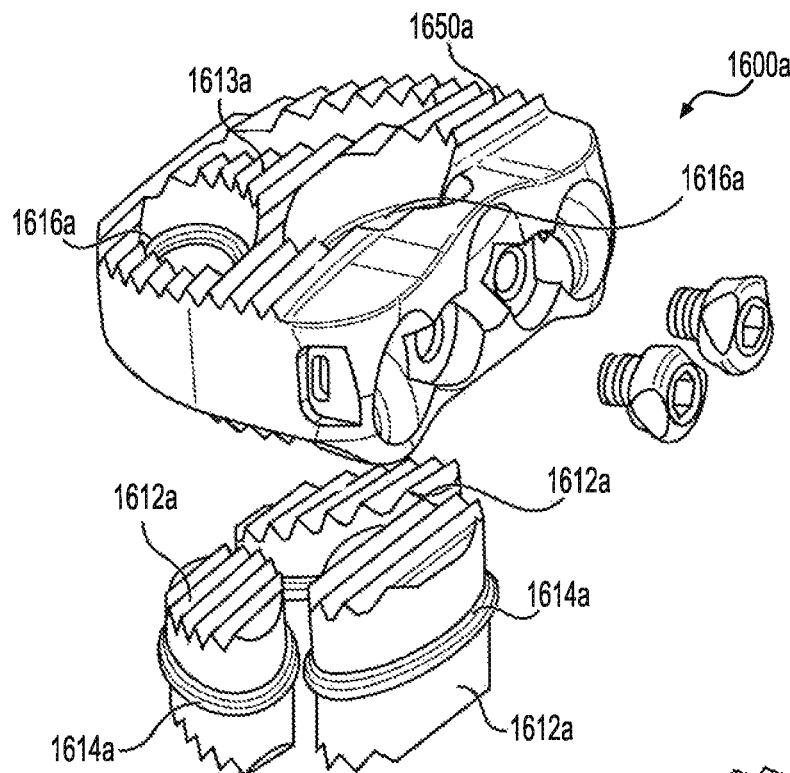
FIGS. 18A and 18B show exploded views of an eighteenth embodiment having a frame with a plurality of endplates configured to be received within the openings in the frame.
Figure 18B:
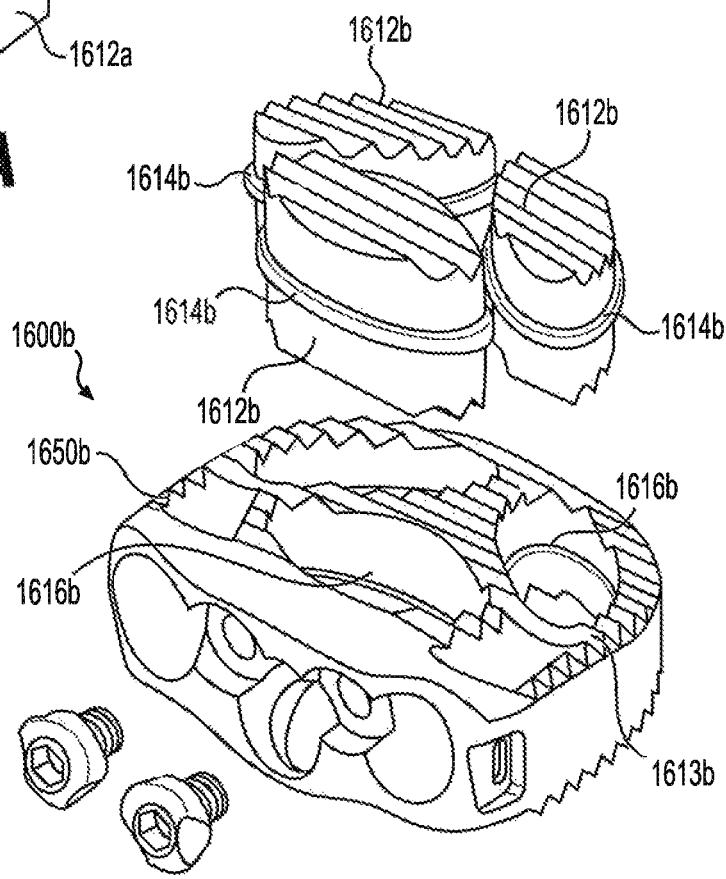

FIGS. 18A and 18B illustrate stand-alone intervertebral implants 1600a, 1600b, which may be suitable for an anterior lumbar procedure. The implants 1600a, 1600b include a spacer or frame 1650a, 1650b and one or more endplates 1612a, 1612b. The endplates 1612a, 1612b may be in the form of PEEK or allograft spacers, for example, sized and configured to fit within the openings in the frame 1650a, 1650b.

The frame 1650a, 1650b includes upper and lower surfaces each having contact areas (e.g., a plurality of protrusions 1613a, 1613b) configured to contact and engage adjacent vertebrae (not shown). The frame 1650a, 1650b may contain one or more openings which extend from the upper surface to the lower surface. The openings may be in the form of oval holes, for example. As shown, three openings may be provided: two posterior openings and one anterior opening. The openings may be configured for receiving bone graft material, for example, to promote fusion of the adjacent vertebral bodies.

In one embodiment, the openings may be configured to receive corresponding endplates 1612a, 1612b. The endplates 1612a, 1612b may be inserted from the top or the bottom of the implant 1600a, 1600b. The endplates 1612a, 1612b may be retained in the openings by a ridge 1614a, 1614b and corresponding slot or groove 1616a, 1616b located on a mid-transverse plane on the implants 1600a, 1600*b*. The ridge 1614*a*, 1614*b* may project around a perimeter of each endplate 1612*a*, 1612*b*. The ridge 1614*a*, 1614*b* may be centrally located between the upper and lower surface of the implant 1600*a*, 1600*b*, but is also envisioned that additional ridges may be provided or the ridge may be offset from the center line.

The endplate 1612*a*, 1612*b* upon insertion has an interference fit and then snaps into the corresponding groove 1616*a*, 1616*b* on the frame 1650*a*, 1650*b*. The endplates 1612*a*, 1612 may be in the shape of ovals although any suitable shape is envisioned. The posterior ovals are substantially the same and are interchangeable. The anterior oval has a distinct feature on its bottom; namely, a slot for the fastener, to distinguish it from the posterior ovals. The endplates 1612*a*, 1612*b* may also include protrusions on the upper and/or lower surfaces which match and align with the protrusions 1613*a*, 1613*b* on the frame 1650*a*, 1650*b*.

The inserts, members, frames, spacers, and endplates described in this document may be comprised of any suitable materials. The spacers or endplates can be comprised of any material that is conducive to the enhancement of fusion between the two adjacent vertebrae. In one particular embodiment, the spacer or endplate is made of a biocompatible plastic, like polyether ether ketone (PEEK), polyetherketoneketone (PEKK), ultra-high molecular weight (UHMW) polyethylene, or other polymers and plastics known in the art which are physiologically compatible. Any other materials that are physiologically compatible may also be used such as bone or metal. The inserts, members, or frames can also be comprised of any physiologically compatible materials. In the preferred embodiment, the inserts, members, or frames are composed of a biocompatible metal, such as stainless steel, titanium, titanium alloys, surgical steel, and metal alloys, for example. Preferably, the inserts, members, or frames are formed from titanium or a titanium alloy. Any other materials that are physiologically compatible may also be used such as bone or plastic.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An intervertebral implant for implantation in an intervertebral space between adjacent vertebrae, the implant comprising:
   a frame comprising a body having an anterior side and a posterior side connected to the anterior side by left and right sides, the body having an interior surface defining at least one through opening;
   at least one spacer configured to be snap-fit into the at least one through opening, an upper surface of the spacer and an upper surface of the body forming an upper surface of the implant configured to be in contact with an endplate of an upper vertebral body;
   wherein the spacer includes a side surface between the upper and lower surfaces and the side surface includes one of a ridge or recess and the interior surface defining at least one through opening includes a side surface including the other of the ridge or recess for the snap fit configuration and
   wherein the frame includes a first hole for receiving a first screw and a second hole for receiving a second screw.

2. The implant of claim 1, wherein the upper surface of the body and the spacer include a plurality of protrusions, and the protrusions of the body aligns with and matches the protrusions of the spacer.

3. The implant of claim 1, wherein the side surface includes the ridge which extends around the entire circumference of the side surface.

4. The implant of claim 1, wherein:
   the upper surface of the body and the spacer include a plurality of protrusions, and the protrusions of the body aligns with and matches the protrusions of the spacer.

5. The implant of claim 1, wherein:
   the at least one through opening includes at least three through openings; and
   the at least one spacer includes at least three spacers and each of the spacers is adapted to snap-fit-into a corresponding through opening.

6. The implant of claim 1, wherein each of the first and second holes extends from the anterior side to the upper surface of the body.

7. The implant of claim 6, wherein the frame includes a third hole for receiving a third screw, and the third hole extends from the anterior side to a lower surface of the body.

8. The implant of claim 7, wherein the spacer is made of PEEK material.

9. The implant of claim 7, wherein the spacer is made of allograft material.

10. The implant of claim 7, further comprising an anti-backout lock disposed on the anterior side for preventing backout of the first bone screw after insertion.

11. The implant of claim 7, further comprising:
    a first anti-backout lock disposed on the anterior side between the first and third holes and adapted to prevent a backout of the first and third bone screw after insertion; and
    a second anti-backout lock disposed on the anterior side between the second and third holes and adapted to prevent a backout of the second and third bone screw after insertion.

12. An intervertebral implant for implantation in an intervertebral space between adjacent vertebrae, the implant comprising:
    a frame comprising a body having an anterior side and a posterior side connected to the anterior side by left and right sides, the body having interior surfaces defining a plurality of through openings;
    a plurality of spacers each configured to be snap-fit into a corresponding through opening, an upper surface of the spacer and an upper surface of the body forming an upper surface of the implant configured to be in contact with an endplate of an upper vertebral body;
    wherein each spacer includes a side surface between the upper and lower surfaces and the side surface includes one of a ridge or recess and the interior surfaces defining the corresponding through opening includes a side surface including the other of the ridge or recess for the snap fit configuration, and
    wherein:
       the frame includes a first hole for receiving a first screw and a second hole for receiving a second screw; and
       each of the first and second holes extends from the anterior side to the upper surface of the body.

13. The implant of claim 12, wherein the upper surface of the body and the spacer include a plurality of protrusions, and the protrusions of the body aligns with and matches the protrusions of the spacer.

14. The implant of claim 13, wherein the side surface includes the ridge which extends around the entirety circumference of the side surface.

15. The implant of claim 12, wherein:
the at least one through opening includes at least three through openings; and
the at least one spacer includes at least three spacers and each of the spacers is adapted to snap-fit-into a corresponding through opening.

16. The implant of claim 12, wherein the frame includes a third hole for receiving a third screw, and the third hole extends from the anterior side to a lower surface of the body.

17. The implant of claim 16, wherein the spacer is made of PEEK material.

* * * * *